(12) United States Patent
Xu et al.

(10) Patent No.: US 9,873,707 B2
(45) Date of Patent: Jan. 23, 2018

(54) METHODS AND INTERMEDIATES FOR PREPARING MACROLACTAMS

(71) Applicant: Merck Sharp & Dohme Corp., Rahway, NJ (US)

(72) Inventors: Feng Xu, Staten Island, NY (US); Richard Desmond, Lebanon, NJ (US); Guy R. Humphrey, Hillsborough, NJ (US); Hongming Li, Westfield, NJ (US); Ji Qi, Beijing (CN); Rebecca T. Ruck, Jersey City, NJ (US); Zhiguo Jake Song, Edison, NJ (US); Tao Wang, Berkeley Heights, NJ (US); Yong-Li Zhong, Edison, NJ (US); Jeonghan Park, Whippany, NJ (US); Laura Marie Artino, Oakhurst, NJ (US); Richard John Varsolona, Scotch Plains, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/029,876

(22) PCT Filed: Oct. 14, 2014

(86) PCT No.: PCT/US2014/060348
§ 371 (c)(1),
(2) Date: Apr. 15, 2016

(87) PCT Pub. No.: WO2015/057611
PCT Pub. Date: Apr. 23, 2015

(65) Prior Publication Data
US 2016/0251375 A1 Sep. 1, 2016

Related U.S. Application Data

(60) Provisional application No. 61/927,701, filed on Jan. 15, 2014, provisional application No. 61/892,790, filed on Oct. 18, 2013.

(51) Int. Cl.
| | |
|---|---|
| *C07C 69/14* | (2006.01) |
| *C07K 5/083* | (2006.01) |
| *C07D 498/16* | (2006.01) |
| *C07C 69/63* | (2006.01) |
| *C07D 403/12* | (2006.01) |
| *C07C 269/04* | (2006.01) |
| *C07C 271/34* | (2006.01) |
| *C07C 231/12* | (2006.01) |
| *C07K 5/062* | (2006.01) |
| *C07C 27/20* | (2006.01) |
| *C07C 29/36* | (2006.01) |
| *C07C 29/58* | (2006.01) |
| *C07C 45/00* | (2006.01) |
| *C07C 45/63* | (2006.01) |
| *C07K 5/12* | (2006.01) |

(52) U.S. Cl.
CPC ............ *C07D 498/16* (2013.01); *C07C 27/20* (2013.01); *C07C 29/36* (2013.01); *C07C 29/58* (2013.01); *C07C 45/00* (2013.01); *C07C 45/63* (2013.01); *C07C 69/14* (2013.01); *C07C 69/63* (2013.01); *C07C 231/12* (2013.01); *C07C 269/04* (2013.01); *C07C 271/34* (2013.01); *C07D 403/12* (2013.01); *C07K 5/06034* (2013.01); *C07K 5/0808* (2013.01); *C07K 5/126* (2013.01); *C07C 2601/02* (2017.05)

(58) Field of Classification Search
CPC ........ A61K 38/06; C07C 69/14; C07C 69/63; C07K 5/0808
See application file for complete search history.

(56) References Cited

U.S. PATENT DOCUMENTS

| | | |
|---|---|---|
| 3,983,243 A | 9/1976 | Pfiffner et al. |
| 6,291,530 B1 | 9/2001 | Greenspan et al. |
| 7,973,040 B2 | 7/2011 | Harper et al. |

FOREIGN PATENT DOCUMENTS

| | | |
|---|---|---|
| EP | 2764866 A1 | 8/2014 |
| WO | WO2006119061 | 11/2006 |
| WO | WO2007015787 | 2/2007 |
| WO | WO2007015855 | 2/2007 |
| WO | WO2007016441 | 2/2007 |
| WO | WO2007131966 | 11/2007 |
| WO | WO2007148135 | 12/2007 |
| WO | WO2008051477 | 5/2008 |
| WO | WO2008051514 | 5/2008 |
| WO | WO2008057208 A2 | 5/2008 |

(Continued)

OTHER PUBLICATIONS

Kevin Cheng et al., Diastereoselective Preparation of Cyclopropanols Using Methylene Bis(iodozinc), 13(9) Organic Letters 2346-49 (2011).
E. J. Corey et al., Catalytic Diastereoselective Synthesis of Cis-1,2-Disubstituted Cyclopropanols from Esters Using a Vicinal Dicarbanion Equivalent, 116 J. Am. Chem. Soc. 9345-46 (1994).
Valerie A. Keller et al., Dioxolane-to-Bridged Acetal-to-Spiroketal via Ring-Closing Metathesis and Rearrangement: A Novel Route to 1,7-Dioxaspiro[5.5]undecanes, 4(3) Org. Lett. 467-70 (2002).
Nigel J. Liverton et al., MK-7009, a Potent and Selective Inhibitor of Hepatitis C Virus NS3/4A Protease, 54(1) Antimicrobial Agents and Chemotherapy 305-311 (Jan. 2010).
Nigel J. Liverton et al., Molecular Modeling Based Approach to Potent P2-P4 Macrocyclic Inhibitors of Hepatitis C NS3/4A Protease, 130(14) J. Am. Chem. Soc. 4607-09 (2008).

(Continued)

*Primary Examiner* — Jeffrey E. Russel
(74) *Attorney, Agent, or Firm* — Julie M. Lake; John C. Todaro

(57) ABSTRACT

The present invention includes compounds useful as intermediates in the preparation of macrolactams, methods for preparing the intermediates, and methods for preparing macrolactams. One use of the methods and intermediates described herein is in the production of macrolactam compounds able to inhibit HCV NS3 protease activity. HCV NS3 inhibitory compounds have therapeutic and research applications.

13 Claims, 11 Drawing Sheets

(56) References Cited

FOREIGN PATENT DOCUMENTS

| WO | WO2008057209 | 5/2008 |
| WO | WO2009010804 | 1/2009 |
| WO | WO2009108507 A1 | 9/2009 |
| WO | WO2009134624 A1 | 11/2009 |
| WO | WO2010011566 A1 | 1/2010 |
| WO | WO2011014487 | 2/2011 |
| WO | WO2013028465 | 2/2013 |
| WO | WO2013028470 A1 | 2/2013 |
| WO | WO2013028471 | 2/2013 |
| WO | WO 2015/095437 A1 * | 6/2015 |

OTHER PUBLICATIONS

Hans-Christian Militzer et al., Versatile Syntheses of Alkynyl- and Substituted Alkynylcyclopropanes: 2-Alkoxyethynylcyclopropanes for the Anellation of Bicyclo[3.3.0]octane Fragments, Synthesis 998-1012 (1993).

Ambarish K. Singh et al., Development of a Practical, Safe, and High-Yielding Process for the Preparation of Enantiomerically Pure trans-Cyclopropane Carboxylic Acid, 6(5) Org. Proc. Res. & Dev. 618-620 (2002).

* cited by examiner

METHODS AND INTERMEDIATES FOR PREPARING MACROLACTAMS

CROSS-REFERENCE TO RELATED APPLICATIONS

This application is a National Stage application of International Patent Application No. PCT/US2014/060348, filed Oct. 14, 2014, which claims priority to U.S. Provisional Patent Application No. 61/927,701, filed Jan. 15, 2014, and U.S. Provisional Patent Application No. 61/892,790, filed Oct. 18, 2013.

FIELD OF THE INVENTION

The present invention relates to process and intermediates that can be used for preparing macrolactams. One use of the methods and intermediates described herein is the production of macrolactam compounds able to inhibit HCV NS3 protease activity. HCV NS3 inhibitory compounds have therapeutic and research applications.

BACKGROUND OF THE INVENTION

Hepatitis C virus (HCV) infection is a major health problem. HCV infection leads to chronic liver disease, such as cirrhosis and hepatocellular carcinoma, in a substantial number of infected individuals.

Several virally-encoded enzymes are putative targets for therapeutic intervention, including a metalloprotease (NS2-3), a serine protease (NS3), a helicase (NS3), and an RNA-dependent RNA polymerase (NS5B). The NS3 protease is located in the N-terminal domain of the NS3 protein. NS4A provides a cofactor for NS3 activity.

Examples of publications describing macrolactam compounds able to inhibit HCV protease activity include: Harper et al., WO 2010/011566; Liverton et al., WO 2009/134624; McCauley et al., WO 2009/108507; Liverton et al., WO 2009/010804; Liverton et al., WO 2008/057209; Liverton et al., WO 2008/051477; Liverton et al., WO 2008/051514; Liverton et al., WO 2008/057208; Crescenzi et al., WO 2007/148135; Di Francesco et al., WO 2007/131966; Holloway et al., WO 2007/015855; Holloway et al., WO 2007/015787; Holloway et al., WO 2007/016441; Holloway et al., WO 2006/119061; Liverton et al., *J. Am. Chem. Soc.* 130: 4607-4609, 2008; and Liverton et al., *Antimicrobial Agents and Chemotherapy* 54:305-311, 2010.

SUMMARY OF THE INVENTION

The present disclosure provides methods and intermediates for preparing macrolactams. One use of the methods and intermediates described herein is in the production of macrolactam compounds able to inhibit HCV NS3 protease activity. HCV NS3 inhibitory compounds have therapeutic and research applications.

In particular, the present disclosure provides a method of preparing a compound of Formula C:

wherein n is selected from the group consisting of 0, 1, 2, 3, 4, 5, 6, 7, and 8; $X^1$ and $X^2$ are each independently selected from the group consisting of Br, Cl, and I; and $R^5$ is selected from the group consisting of $C_{1-8}$ alkyl, $C_{3-8}$ cycloalkyl, aryl, and heteroaryl groups and $R^5$ is substituted by 0, 1, 2, 3, or 4 substituents independently selected from the group consisting of $C_{1-6}$ alkyl, —$C_{2-6}$ alkenyl,—$C_{2-6}$ alkynyl, aryl, halogen, —$NH_2$ and —OH. The method comprises the steps of (1) reacting

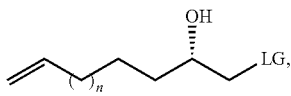

where LG is selected from the group consisting of halogen atoms, —O—$SO_2R^8$, —O—$PO(OR^8)_2$ or a protecting group and each $R^8$ is independently selected from the group consisting of $C_{1-8}$ alkyl, $C_{3-8}$ cycloalkyl, aryl, and heteroaryl groups and each $R^8$ is independently substituted by 0, 1, 2, 3, or 4 substituents independently selected from the group consisting of $C_{1-6}$ alkyl, —$C_{2-6}$ alkenyl, alkynyl, aryl, halogen, —$NH_2$; and —OH, and the protecting group is selected from —$OSiR^8$ and —$OR^8$, with a chiral alcohol and

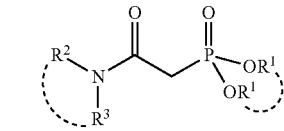

to produce

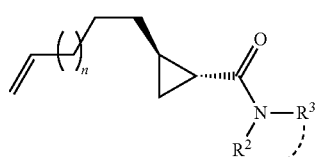

where each $R^1$ is independently selected from the group consisting of $C_{1-8}$ alkyl, aryl, and heteroaryl groups, or two $R^1$ are taken, together with the O—P—O atoms to which they are attached, to form a ring containing 5-19 atoms; and where $R^2$ and $R^3$ are each selected from the group consisting of H, $C_{1-8}$ alkyl, and —O—$C_{1-8}$ alkyl groups, or where $R^2$ is H, and $R^3$ is a —O—$C_{1-8}$ alkyl group, or $R^2$ and $R^3$ are each H or $C_{1-8}$ alkyl groups or are taken together with the nitrogen atom to which they are attached to form a ring containing 5-19 atoms; (2) reacting

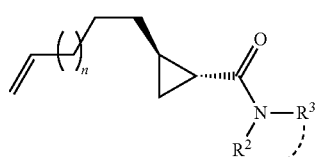

with a Grignard reagent to produce

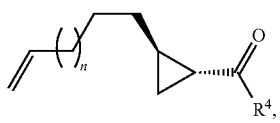

where $R^4$ is selected from the group consisting of $C_{1-8}$ alkyl, substituted $C_{1-8}$ alkyl, aryl, substituted aryl, heteroaryl, and substituted heteroaryl groups and $R^4$ is substituted by 0, 1, 2, 3, or 4 substituents independently selected from the group consisting of $C_{1-6}$ alkyl, $C_{2-6}$, alkenyl, $C_{2-6}$ alkynyl, aryl, halogen, —$NH_2$ and —OH; (3) halogenating

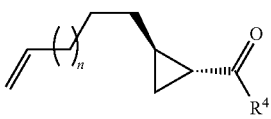

to produce

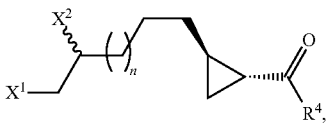

where $X^1$ and $X^2$ are each independently selected from the group consisting of Br, Cl, and I; and (4) oxidizing

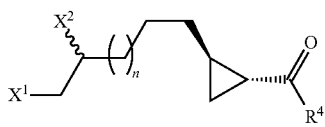

to produce oxygen-inserted compounds

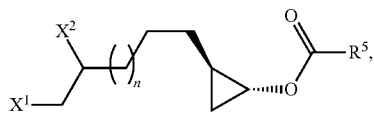

where $R^5$ is selected from the group consisting of $C_{1-8}$ alkyl, $C_{3-8}$ cycloalkyl, aryl, and heteroaryl groups and $R^5$ is substituted by 0, 1, 2, 3 or 4 substituents independently selected from the group consisting of $C_{1-6}$ alkyl, $C_{1-6}$ alkenyl, $C_{1-6}$ alkynyl, aryl, halogen, —$NH_2$ and —OH.

In addition, the present disclosure provides a method of preparing a compound of Formula B:

or a salt thereof, wherein n, $R^7$, and $R^6$ are as described above. The method comprises preparing a compound of Formula C according to the method of claim 1; and converting

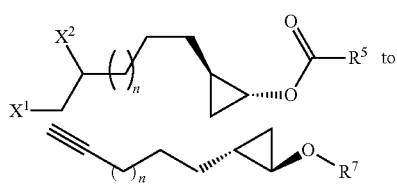

or a salt thereof. The compounds of Formula B may be prepared by making compounds of Formula C and converting the compounds of C into compounds of Formula B.

Other embodiments, aspects and features of the present invention are either further described in or will be apparent from the ensuing description, examples and appended claims.

DETAILED DESCRIPTION OF THE INVENTION

Figure 1:
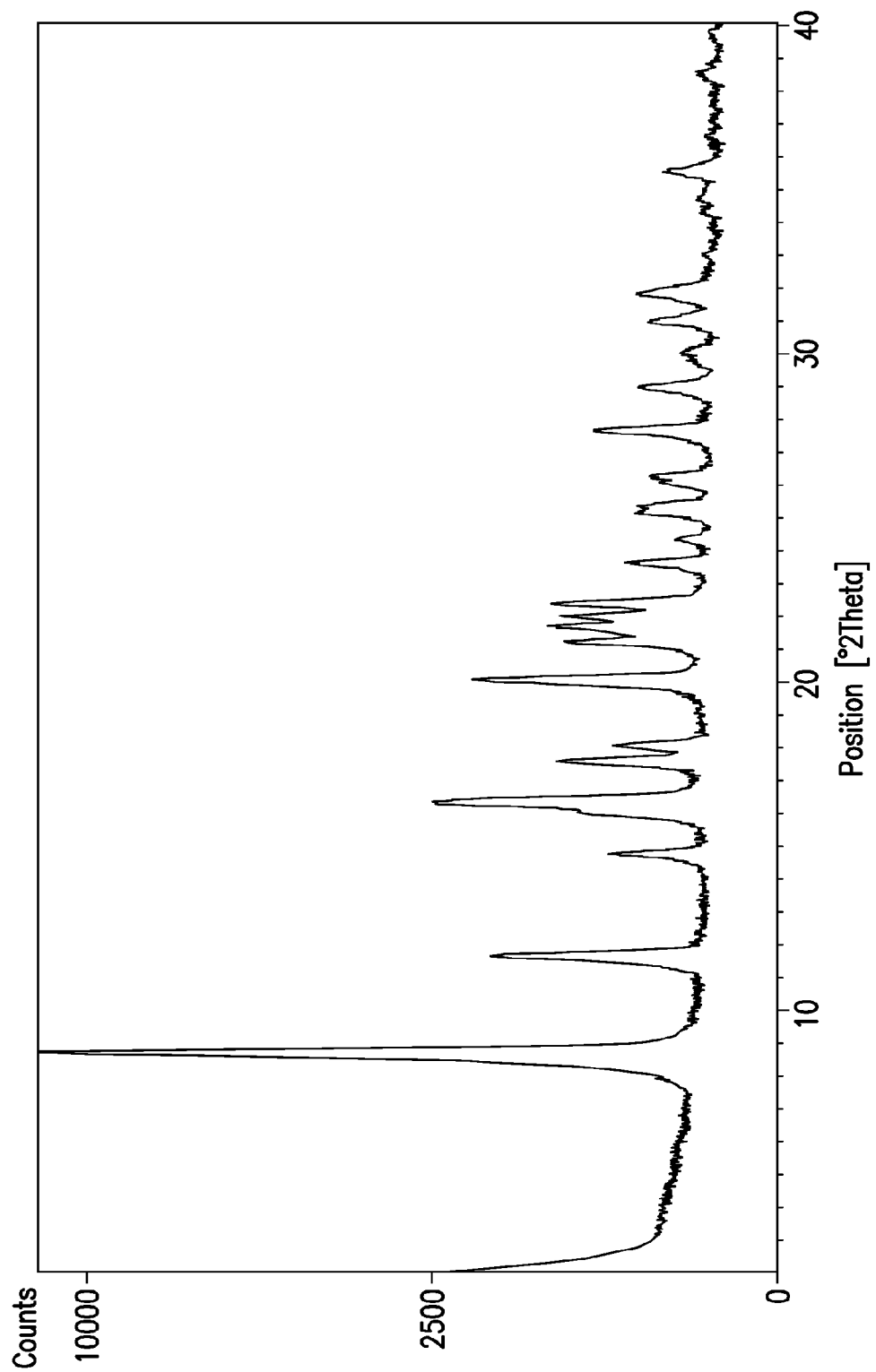
FIG. 1 provides a characteristic X-ray diffraction pattern for the crystalline tert-butylamine salt of the alkyne acid of Example 10.

Macrolactam compounds able to inhibit HCV activity have different uses including inhibiting HCV activity in vivo, inhibiting HCV activity in vitro, and inhibiting HCV NS3 enzymatic activity. In vivo inhibition of HCV activity can be used for therapeutic applications. Inhibiting HCV activity in vitro has different applications including being used to obtain HCV resistant mutants, further characterizing the ability of a functional group to inhibit HCV replicon or enzymatic activity, and studying HCV replication or protease activity.

The methods and intermediates described herein can be used to synthesize macrolactams, such as Compound A and compounds varying from Compound A by one or more functional group. Compound A has the following structure:

Compound A

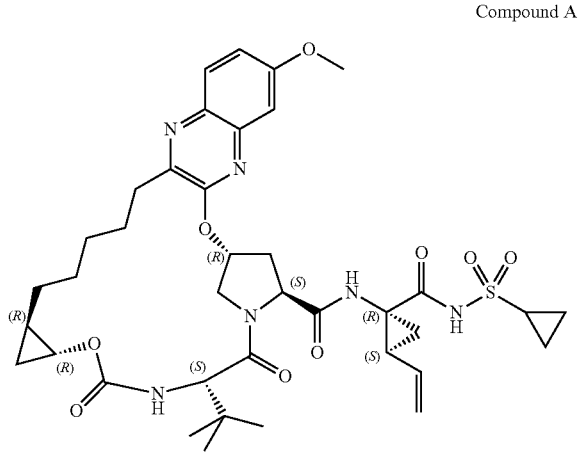

Functional groups that can be modified include a different heterocycle group, a different alkyl in place of the tert-butyl group, and alteration of the cyclopropylsulfonyl functional group and the cyclopropyl amide moiety (e.g., with an ethyl group replacing the ethylene and/or a methylcyclopropyl group replacing the cyclopropyl group).

Different intermediates and synthesis protocols are illustrated herein where Compound A was ultimately obtained. However, it is understood that based on the guidance provided herein other macrolactams can be produced using appropriate intermediates and by adding or modifying different functional groups. Examples of different macrolactams having different functional groups are provided in McCauley et al., WO 2011/014487; Harper et al., WO 2010/011566; Liverton et al., WO 2009/134624; McCauley et al., WO 2009/108507; Liverton et al., WO 2009/010804; Liverton et al., WO 2008/057209; Liverton et al., WO 2008/051477; Liverton et al., WO 2008/051514; Liverton et al., WO 2008/057208; Crescenzi et al., WO 2007/148135; Di Francesco et al., WO 2007/131966; Holloway et al., WO 2007/015855; Holloway et al., WO 2007/015787; Holloway et al., WO 2007/016441; Holloway et al., WO 2006/119061; Liverton et al., *J. Am. Chem. Soc.*, 130:4607-4609, 2008; and Liverton et al., *Antimicrobial Agents and Chemotherapy* 54:305-311, 2010.

Harper et al., WO 2010/011566 describes an alternative method for making Compound A. Harper et al., WO 2010/011566, also includes data illustrating the ability of Compound A to inhibit HCV replicon activity and NS3/4A. In addition, Yasuda et al., WO 2013/028471 and Xu et al., WO 2013/028470 describe methods and intermediates for making Compound A, and Beutner et al., WO 2013/028465 describes crystal forms of Compound A.

Intermediates and procedures that can be used to produce macrolactams can be illustrated by taking into account: (1) cyclopropyl linker synthesis: (2) heterocycle synthesis; and (3) forming a macrolactam using the cyclopropyl linker and heterocycle group, and optionally adding or modifying different functional groups. The optionally added functional groups can be used to provide for, or enhance, the ability of a compound to inhibit HCV NS3 activity and/or HCV replication.

Cyclopropyl Linker Synthesis

Cyclopropyl linker intermediates useful for preparing Compound A and analogues thereof include compounds of Formula B,

wherein n is selected from the group consisting of 0, 1, 2, 3, 4, 5, 6, 7 and 8; and $R^7$ is selected from the group consisting of acetyl and

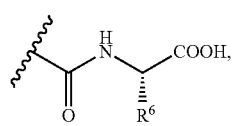

in which $R^6$ is selected from the group consisting of $C_{1-8}$ alkyl, $C_{3-8}$ cycloalkyl, aryl and heterocycle groups. In embodiments, the compound of Formula B is a compound in which $R^7$ is acetyl. In separate embodiments, the compound of Formula B is a compound in which $R^7$ is

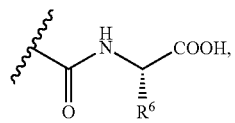

and $R^6$ is selected from the group consisting of $C_2$-$C_6$ alkyl groups. In particular embodiments, the compound of Formula B is a compound in which $R^7$ is

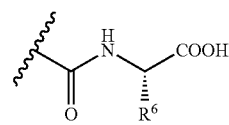

and $R^6$ is tert-butyl; that is, the compound of Formula B is (S)-3,3-dimethyl-2-(((1R,2R)-2-(pent-4-ynyl)cyclopropoxy) carbonylamino) butonic acid, Compound B1:

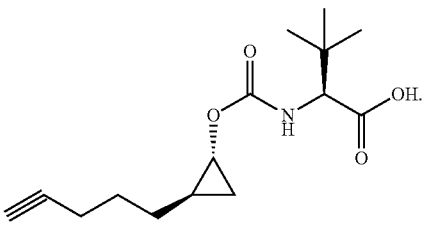 [SMILES: C#CCCC[C@@H]1C[C@H]1OC(=O)N[C@H](C(=O)O)C(C)(C)C]

Scheme A illustrates an overall scheme that can be used to prepare compounds of Formula B, particularly Compound B1, and different intermediates. Each of the individual steps of Scheme A provides for embodiments, and combinations of steps together provide additional embodiments. Further embodiments include steps upstream and downstream from a particular step, such as those illustrated by the Examples.

Unless specifically indicated, any variable maintains its definition as provided in an earlier structure when that variable is used in a later structure.

Scheme A

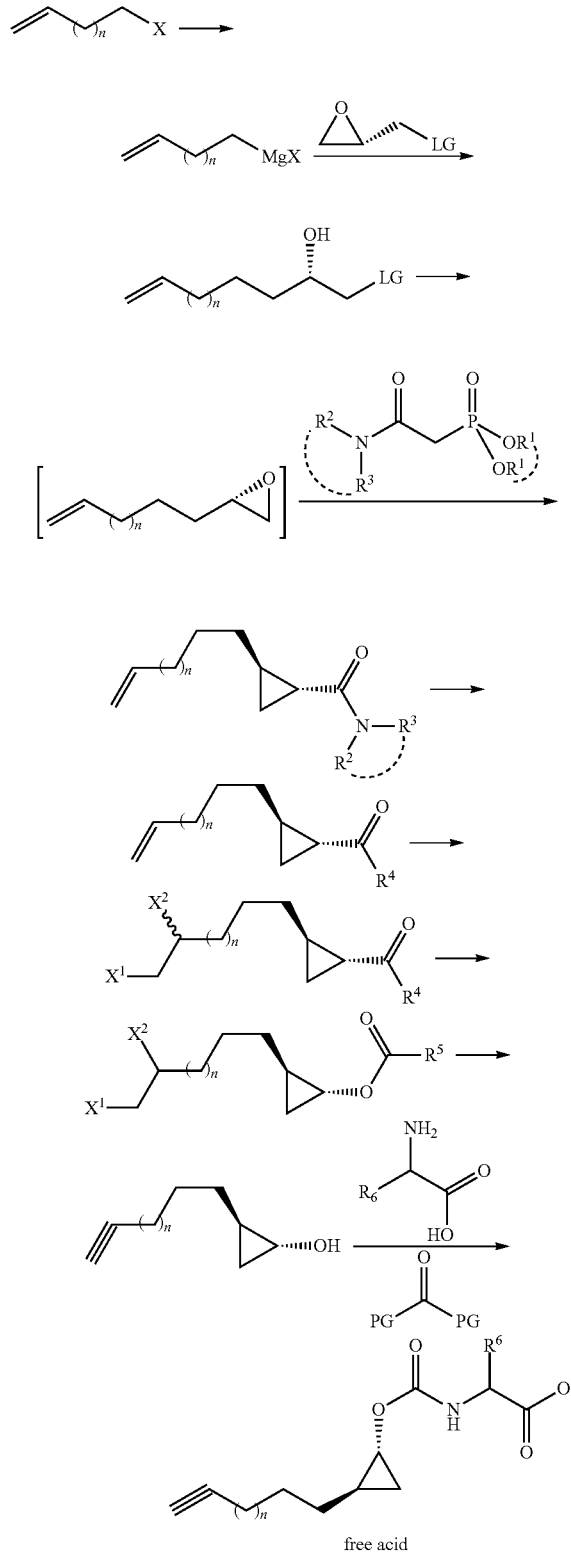

free acid

In the compounds and intermediates of Scheme A, n is 0, 1, 2, 3, 4, 5, 6, 7 or 8.

In the compounds and intermediates of Scheme A,

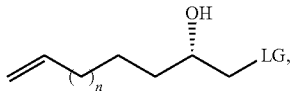

where LG is selected from the group consisting of halogen atoms, —O—SO$_2$R$^8$, —O—PO(OR$^8$)$_2$, and a protecting group, and each R$^8$ is independently selected from the group consisting of C$_{1-8}$ alkyl, C$_{3-8}$ cycloalkyl, aryl, and heteroaryl groups, and the protecting group is selected from —OSiR and —OR$^8$, is prepared by (i) reacting

with a magnesium source to produce

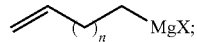

and (ii) reacting

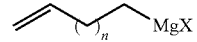

with

to produce

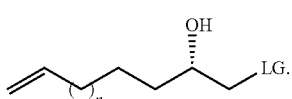

In the compounds and intermediates of Scheme A, X is selected from the group consisting of halogen atoms. Preferably, X is selected from the group consisting of Br, Cl, and F. In specific embodiments, X is Br.

In the compounds and intermediates of Scheme A, LG is a leaving group selected from the group consisting of halogen atoms, —O—S$_2$R$^8$, —O—PO(OR$^8$)$_2$ and a protecting group, where each R$^8$ is independently selected from the group consisting of C$_1$-C$_8$ alkyl, C$_3$-C$_8$ cycloalkyl, aryl and heteroaryl groups, and the protecting group is selected from —O—SiR$^8$ and —O—R$^8$. In embodiments, LG is a leaving group selected from the group consisting of halogens, mesylate

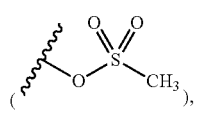

—O—PO(OR$^8$)$_2$, tosylate

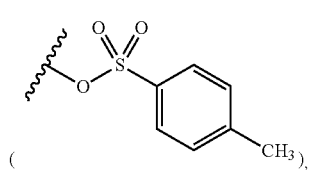

—OCH$_2$OCH$_3$ and —OSiR$^8$$_3$, where each R$^8$ is independently selected from the group consisting of C$_1$-C$_8$ alkyl. It will be understood that a protecting group may be converted to an appropriate leaving group, directly or indirectly (such as by stepwise conversion), to achieve the desired downstream chemistry. In specific embodiments, LG is selected from the group consisting of Br, Cl, F, mesylate and tosylate. In particular embodiments, LG is Cl.

In the compounds and intermediates of Scheme A, PG is a leaving group to promote carbamate bond formation via coupling alcohol intermediate with an amino acid. PG may be selected from imidazoyl and succinimidyl. The coupling may be carried out, in embodiments, with promoters or additives, such as 2-hydroxypyridine-N-oxide (HOPO), hydroxyl succinimide (HOSu), imidazole and imidazole HCl salt.

In embodiments, the third step illustrated in Scheme A employs a chiral alcohol, such as chlorohydrin.

In the compounds and intermediates of Scheme A, each R$^1$ is independently selected from the group consisting of C$_1$-C$_8$ alkyl, aryl and heteroaryl groups. In embodiments, the two R$^1$ are taken, together with the O—P—O atoms to which they are attached, to form a ring. In particular embodiments, each R$^1$ is independently selected from the group consisting of C$_1$-C$_8$ alkyl groups. In specific embodiments, each R$^1$ is independently ethyl.

In the compounds and intermediates of Scheme A, R$^2$ and R$^3$ are each selected from the group consisting of H, —O—C$_1$-C$_8$ alkyl and C$_1$-C$_8$ alkyl groups. In embodiments, R$^2$ is H, and R$^3$ is —O—C$_1$-C$_8$ alkyl, or R$^2$ and R$^3$ are H or C$_1$-C$_8$ alkyl and are taken together with the nitrogen atom to which they are attached to form a ring. In particular embodiments, R$^2$ and R$^3$ are each methyl.

In particular embodiments, R$^1$ is independently ethyl and R$^2$ and R$^3$ are each methyl, such that

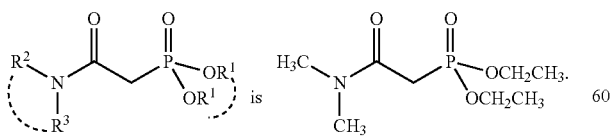

In the compounds and intermediates of Scheme A, R$^4$ is selected from the group consisting of H, C$_1$-C$_8$ alkyl, substituted C$_1$-C$_8$ alkyl, aryl, substituted aryl, heteroaryl and substituted heteroaryl groups.

In the compounds and intermediates of Scheme A, X$^1$ and X$^2$ are each independently selected from the group consisting of Br, Cl and I.

In the compounds and intermediates of Scheme A, R$^5$ and R$^6$ are independently selected from the group consisting of H, C$_1$-C$_8$ alkyl and C$_3$-C$_8$ cycloalkyl groups. In embodiments, R$^5$ and R$^6$ are independently selected from the group consisting of C$_2$-C$_6$ alkyl groups. In particular embodiments, R$^5$ is methyl. In particular embodiments R$^6$ is tert-butyl.

In embodiments, the step of converting

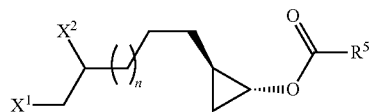

(compounds of Formula C) to

or a salt thereof, is accomplished by the steps of (i) dehalogenating

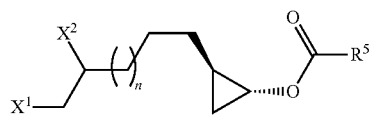

to produce

(ii) reacting

with a reagent containing a leaving group to produce

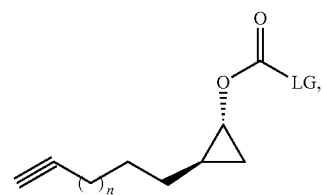

where LG is a leaving group; and (iii) reacting

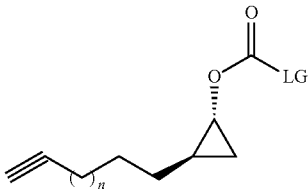

with a reagent selected from carboimide groups and

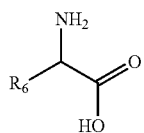

to produce

and (iv) optionally forming a salt of

In some embodiments, the product compound is converted to a pharmaceutically acceptable salt, such as a tert-butylamine salt, dibenzylamine salt or dicyclohexyl amine salt.

Scheme B illustrates an overall scheme that can be used to prepare Compound B1 and different intermediates. Each of the individual steps of Scheme B provides for embodiments, and combinations of steps together provide additional embodiments. Further embodiments include steps upstream and downstream from a particular step, such as those illustrated by the Examples.

Scheme B

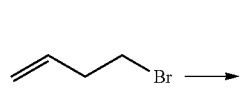

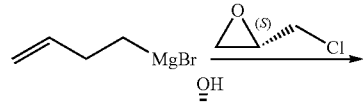

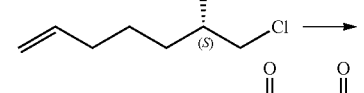

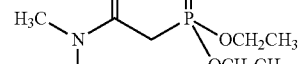

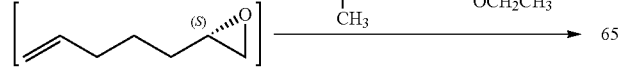

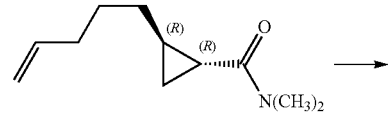

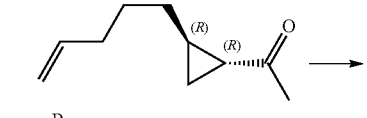

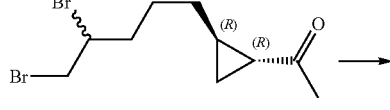

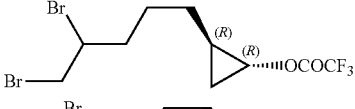

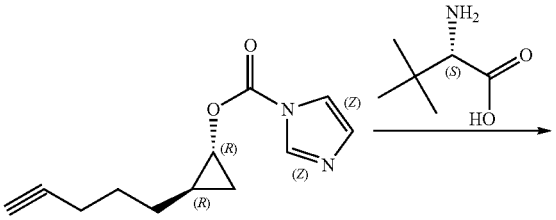

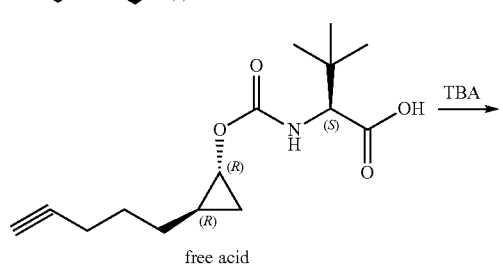

free acid

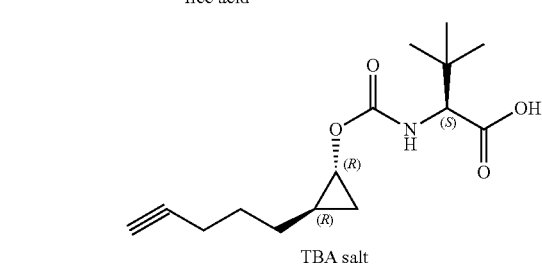

TBA salt

In particular embodiments, the method of Scheme B comprises the steps of (1) reacting with a magnesium source to produce
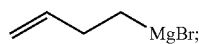
(2) reacting
with
to produce
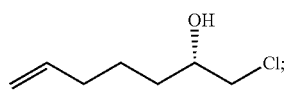
(3) reacting
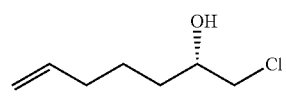
with chlorohydrin and
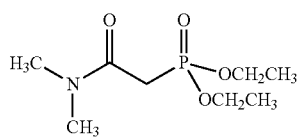
to produce
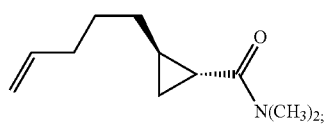
(4) reacting
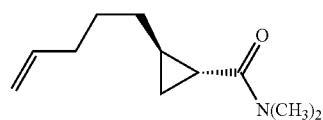
with a Grignard reagent to produce
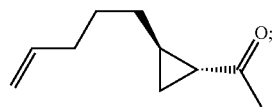
(5) brominating
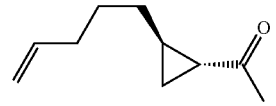
to produce
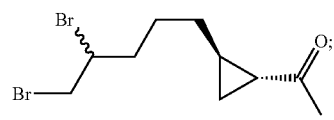
(6) oxidizing
to produce
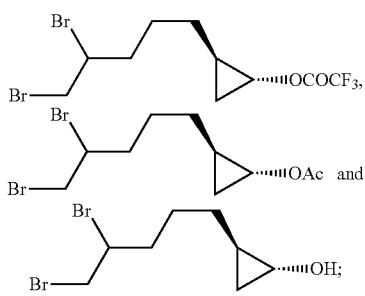
(7) de-brominating
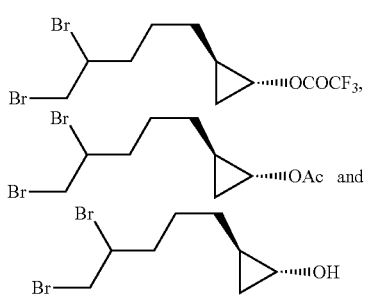

to produce

(8) reacting

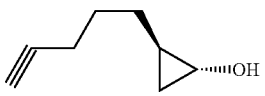

with

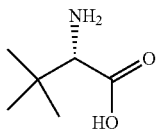

to produce

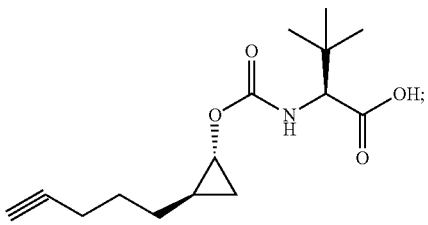 [SMILES: C#CCCC[C@@H]1C[C@H]1OC(=O)N[C@H](C(=O)O)C(C)(C)C]

and (9) optionally forming a salt of

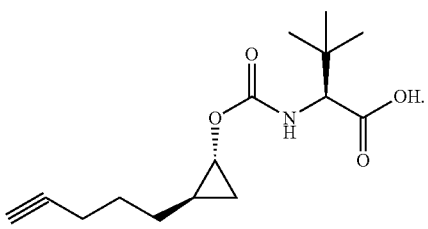 [SMILES: C#CCCC[C@@H]1C[C@H]1OC(=O)N[C@H](C(=O)O)C(C)(C)C]

The compounds in Scheme A and Scheme B are in the neutral form unless otherwise indicated.

Potential advantages of performing the different steps illustrated in Scheme A and Scheme B, compared with a method of producing an alternative cyclopropyl linker having an ethylene group, described in Harper et al., WO 2010/011566, include the possibility of increased efficiency and cost-effectiveness, as well as the possibility of higher overall yields when compared to prior processes, including the methods described in Yasuda et al., WO 2013/028471, and Xu et al., WO 2013/028470. The process provided herein is an asymmetric synthesis, which applies a novel cyclopropanation reaction with a chiral chlorohydrin. Optically pure cyclopropanol intermediates are obtained through a Baeyer-Villiger oxidation. In contrast, the previously described processes are racemic synthesis processes, which require use of selective enzymatic hydrolysis of racemic intermediates.

Carbamate bonds may be formed by use of coupling reagents, such as N,N'-disuccinmidyl carbonate (DSC) and carbonyl diimidazole (CDI) and the like, as previously described, such as in Yasuda et al., WO 2013/028471, and Xu et al., WO 2013/028470. The introduction of promoters or additives, such as 2-hydroxypyridine-N-oxide (HOPO), hydroxyl succinimide (HOSu), imidazole and imidazole HCl salt, may provide improvements to the reaction profile, reaction rate and yield.

Compounds

The term "alkyl" refers to a monovalent straight or branched chain, saturated aliphatic hydrocarbon radical having a number of carbon atoms in the specified range. Thus, for example, "$C_{1-6}$ alkyl" refers to any of the hexyl alkyl and pentyl alkyl isomers as well as n-, iso-, sec- and tert-butyl, n- and iso-propyl, ethyl, and methyl. As another example, "$C_{1-4}$ alkyl" refers to n-, iso-, sec- and tert-butyl, n- and isopropyl, ethyl, and methyl.

The term "cycloalkyl" refers to any monocyclic ring of an alkane having a number of carbon atoms in the specified range. Thus, for example, "$C_{3-8}$ cycloalkyl" (or "$C_3$-$C_8$ cycloalkyl") refers to cyclopropyl, cyclobutyl, cyclopentyl, cyclohexyl, cycloheptyl, and cyclooctyl.

The term "halogen" (or "halo") refers to fluorine, chlorine, bromine and iodine (alternatively referred to as fluoro, chloro, bromo, and iodo or F, Cl, Br and I).

The term "haloalkyl" refers to an alkyl group as defined above in which one or more of the hydrogen atoms have been replaced with a halogen (i.e., F, Cl, Br or I). Thus, for example, "$C_{1-6}$ haloalkyl" (or "$C_1$-$C_6$ haloalkyl") refers to a $C_1$ to $C_6$ linear or branched alkyl group as defined above with one or more halogen substituents. The term "fluoroalkyl" has an analogous meaning except the halogen substituents are restricted to fluoro. Suitable fluoroalkyls include the series $(CH_2)_{0-4}CF_3$ (i.e., trifluoromethyl, 2,2,2-trifluoroethyl, 3,3,3-trifluoro-n-propyl, etc.).

The term "aryl" as a group or part of a group means phenyl or naphthyl.

The term "heteroaryl" as a group or part of a group means a 5- or 6-membered aromatic ring having 1, 2 or 3 heteroatoms selected from N, O and S, attached through a ring carbon or nitrogen. Examples of such groups include pyrrolyl, furanyl, thienyl, pyridyl, pyrazolyl, imidazolyl, oxazolyl, isoxazolyl, thiazolyl, isothiazolyl, pyrazinyl, pyrimidinyl, pyridazinyl, triazolyl, oxadiazolyl, thiadiazolyl, triazinyl and tetrazolyl.

As used herein, any alkyl group, cycloalkyl group, aryl group or heteroaryl group may be substituted, as indicated, by 0, 1, 2, 3, or 4 substituents independently selected from the group consisting of $C_{1-6}$ alkyl, $C_{1-6}$ alkenyl, $C_{1-6}$ alkynyl, aryl, halogen, —$NH_2$, and —OH.

The atoms in a compound described herein may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of described herein. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples.

Isotopically-enriched compounds described herein can be prepared without undue experimentation by conventional techniques well known to those skilled in the art or by processes analogous to those described in the Schemes and Examples provided herein using appropriate isotopically-enriched reagents and/or intermediates.

Compound Forms

Additional embodiments include compounds prepared by the methods disclosed herein. Particular embodiments include compounds selected from the group consisting of

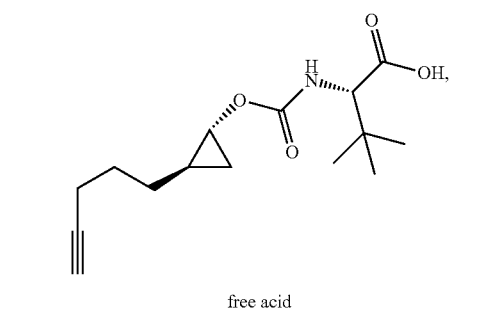

(a)

free acid

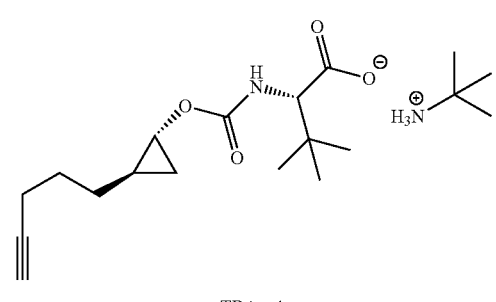

(b)

TBA salt

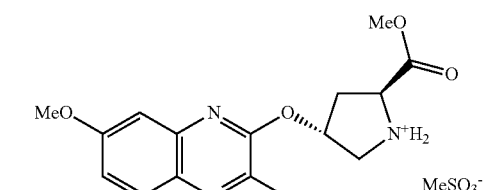

(c)

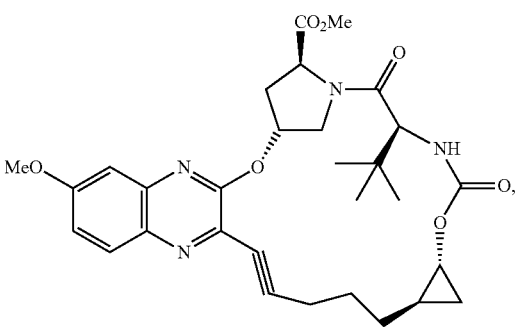

(d)

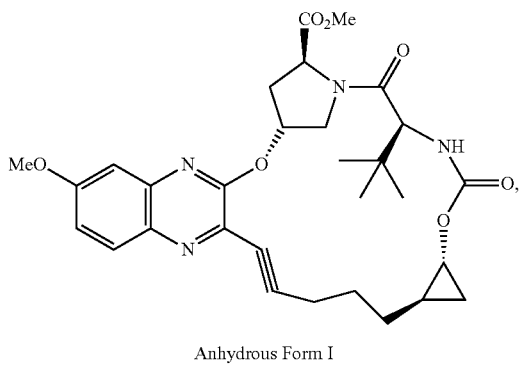

(e)

Anhydrous Form I

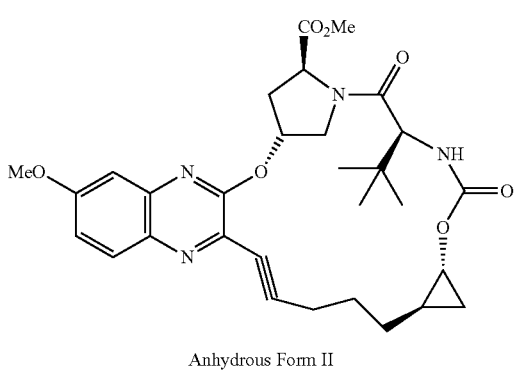

(f)

Anhydrous Form II and

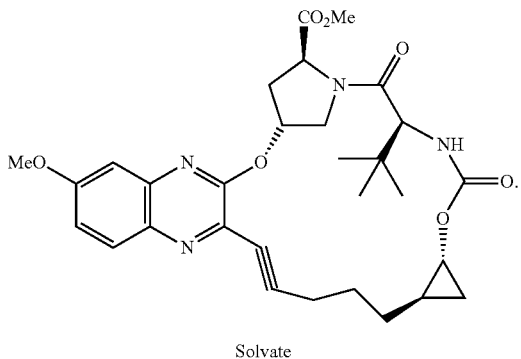

(g)

Solvate

A first compound embodiment is directed to

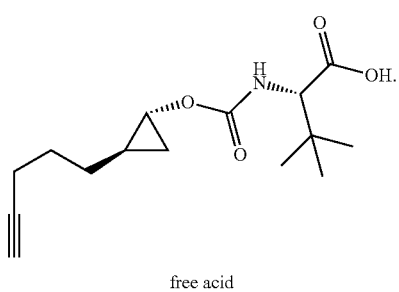 [SMILES: C#CCCC[C@@H]1C[C@H]1OC(=O)N[C@H](C(=O)O)C(C)(C)C]

free acid

In an aspect of the first compound embodiment,

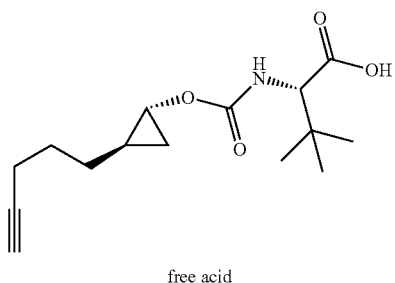 [SMILES: C#CCCC[C@@H]1C[C@H]1OC(=O)N[C@H](C(=O)O)C(C)(C)C]

free acid is substantially pure. Reference to "substantially pure" herein means the particular form makes up at least 50% of the compound present.

A second compound embodiment is directed to

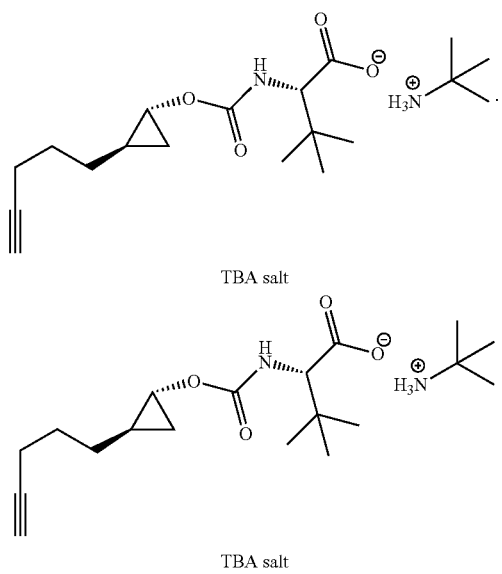

TBA salt is characterized by an X-ray powder diffraction pattern obtained using copper $K_\alpha$ radiation (i.e., the radiation source is a combination of Cu $K_{\alpha 1}$ and $K_{\alpha 2}$ radiation), which comprises three or more characteristic peaks. Characteristic peaks are illustrated in FIG. 1.

In a first aspect of the second compound embodiment,

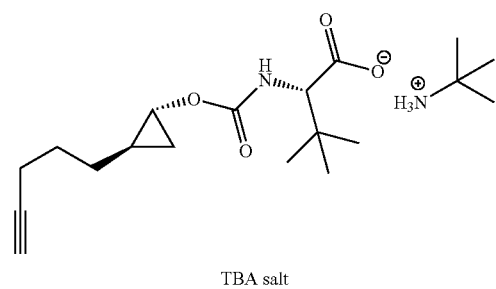

TBA salt is characterized by an X-ray powder diffraction pattern obtained using copper $K_\alpha$ radiation that comprises 2Θ values in degrees of about 2Θ values (i.e., reflections at 2Θ values) in degrees of about 8.8, 11.7, and 20.1.

Reference to "about" with respect to 2Θ values provided herein indicates ±0.1. In this embodiment and analogous embodiments that follow, the term "about" is understood to modify each of the 2Θ values; e.g., the expression "about 8.8, 11.7, and 20.1" is short-hand for "about 8.8, about 11.7, and about 20.1".

In a second aspect of the second compound embodiment,

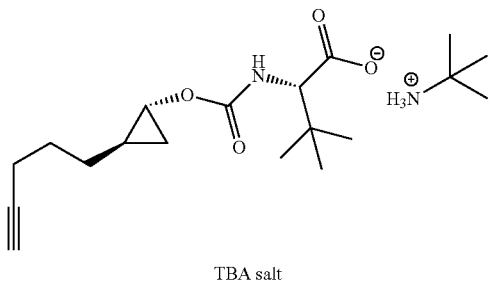

TBA salt is characterized by an X-ray powder diffraction pattern obtained using copper $K_\alpha$ radiation that comprises 2Θ values in degrees of about 2Θ values (i.e., reflections at 2Θ values) in degrees of about 8.8, 11.7, 14.8, 20.1, 23.7, and 27.7.

In a third aspect of the second compound embodiment,

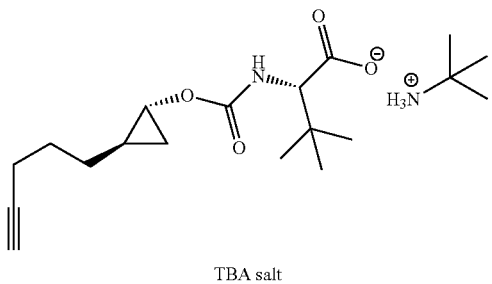

TBA salt is characterized by an X-ray powder diffraction pattern obtained using copper $K_\alpha$ radiation that comprises 2Θ values in degrees of about 2Θ values (i.e., reflections at 2Θ values) in degrees of about 8.8, 11.7, 14.8, 20.1, 23.7, 27.7, 29.0, 31.0 and 31.8.

In a fifth embodiment,

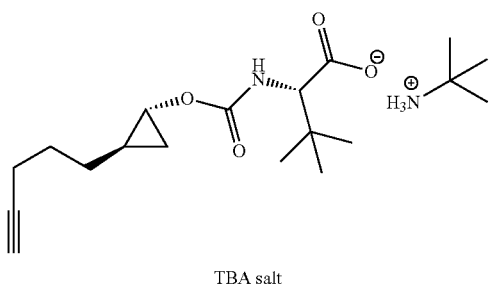

TBA salt is substantially pure.

A third compound embodiment is directed to

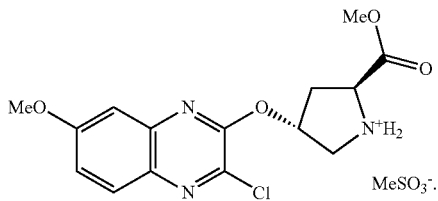

Figure 2:
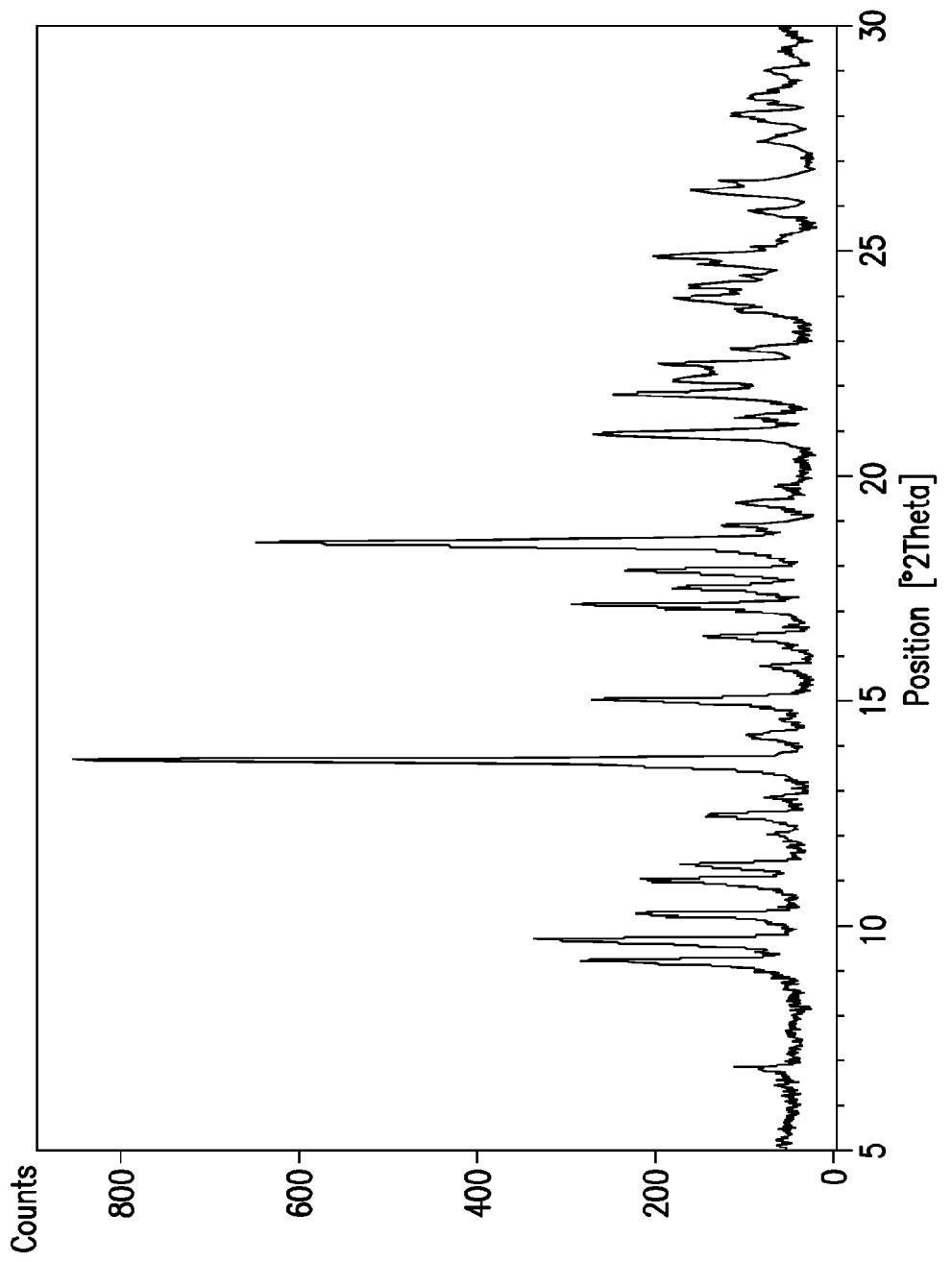
FIG. 2 provides a characteristic X-ray diffraction pattern for the methanesulfonate salt of (2S,4R)-4-(3-chloro-7-methoxyquinoxalin-2-yloxy)-2-(methoxycarbonyl)pyrrolidine of Example 13

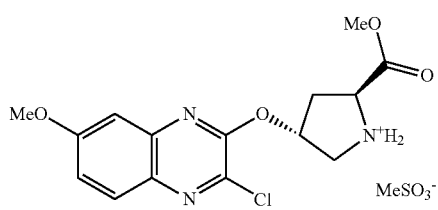

is characterized by an X-ray powder diffraction pattern obtained using copper $K_\alpha$ radiation (i.e., the radiation source is a combination of Cu $K_{\alpha 1}$ and $K_{\alpha 2}$ radiation), which comprises three or more characteristic peaks. Characteristic peaks are illustrated in FIG. 2.

In a first aspect of third compound embodiment,

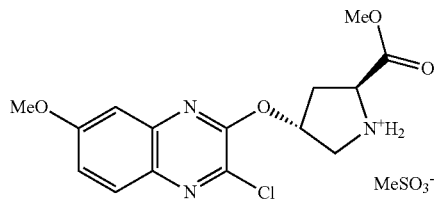

is characterized by an X-ray powder diffraction pattern obtained using copper $K_\alpha$ radiation that comprises 2Θ values in degrees of about 2Θ values (i.e., reflections at 2Θ values) in degrees of about 9.7, 13.7 and 18.5.

In a second aspect of the third compound embodiment,

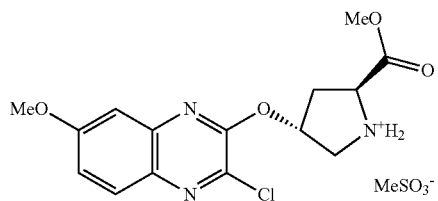

is characterized by an X-ray powder diffraction pattern obtained using copper $K_\alpha$ radiation that comprises 2Θ values in degrees of about 2Θ values (i.e., reflections at 2Θ values) in degrees of about 9.2, 9.7, 13.7, 15.0, 17.1, and 18.5.

In a third aspect of the third compound embodiment,

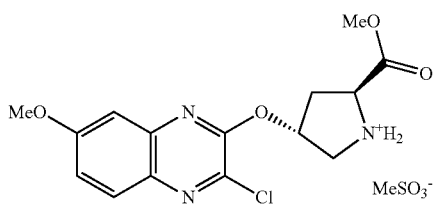

is characterized by an X-ray powder diffraction pattern obtained using copper $K_\alpha$ radiation that comprises 2Θ values in degrees of about 2Θ values (i.e., reflections at 2Θ values) in degrees of about 9.2, 9.7, 10.3, 13.7, 15.0, 17.1, 17.9, 18.5 and 20.9.

In a fourth aspect of the third compound embodiment,

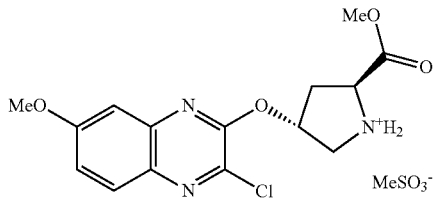

is substantially pure.

A fourth compound embodiment is directed to

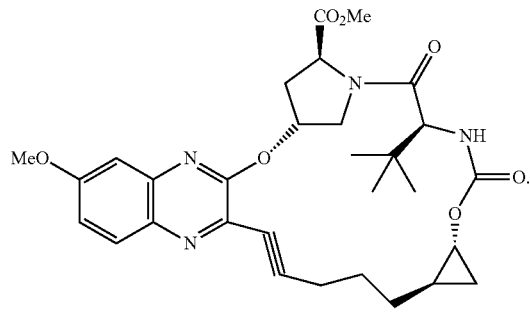

In a fifth aspect of the fourth compound embodiment,

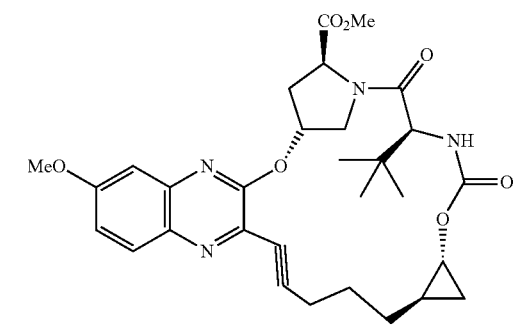

is substantially pure.

A fifth compound embodiment is directed to Anhydrous Form I of

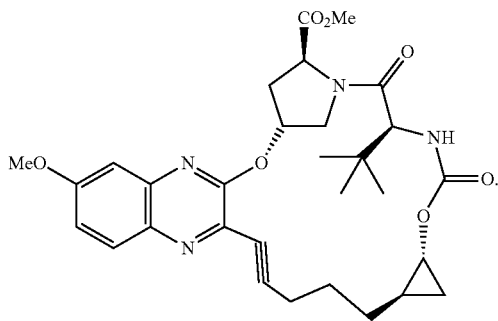

Figure 4:
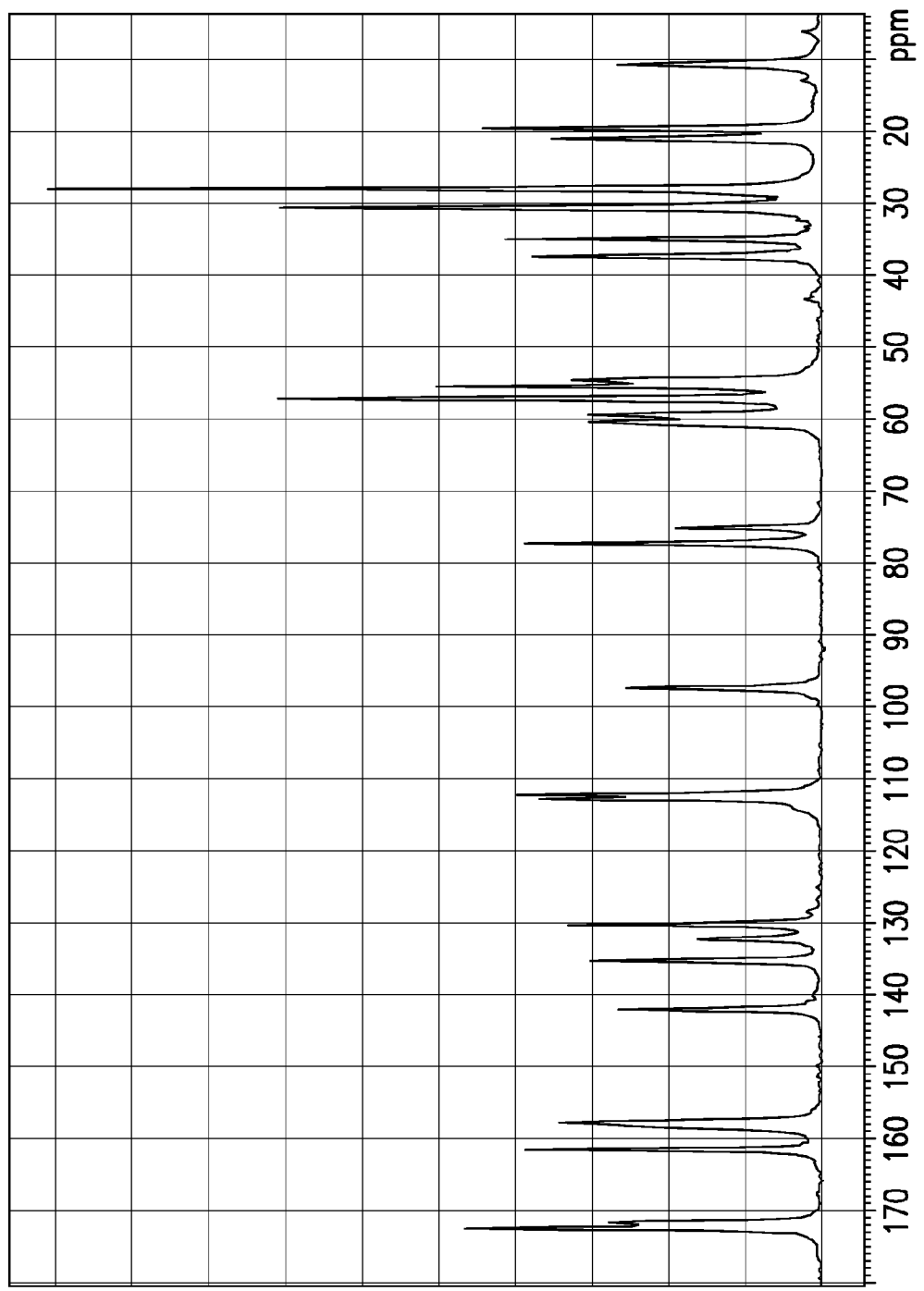
FIG. 4 provides a characteristic $^{13}C$ NMR spectrum for the crystalline macrocyclic alkyne ester anhydrous form I of Example 14A.

Anhydrous Form I is characterized by an X-ray powder diffraction pattern obtained using copper $K_\alpha$ radiation (i.e., the radiation source is a combination of Cu $K_{\alpha 1}$ and $K_{\alpha 2}$ radiation), which comprises three or more characteristic peaks. Characteristic peaks are illustrated in FIG. 4.

In a first aspect of the fifth compound embodiment, Anhydrous Form I is characterized by an X-ray powder diffraction pattern obtained using copper $K_\alpha$ radiation that comprises 2Θ values in degrees of about 2Θ values (i.e., reflections at 2Θ values) in degrees of about 8.7, 13.4, and 20.3.

In a second aspect of the fifth compound embodiment, Anhydrous Form I is characterized by an X-ray powder diffraction pattern obtained using copper $K_\alpha$ radiation that comprises 2Θ values in degrees of about 2Θ values (i.e., reflections at 2Θ values) in degrees of about 5.0, 8.7, 10.1, 13.4, 15.1, 17.6, and 20.3.

In a third aspect of the fifth compound embodiment, Anhydrous Form I is characterized by an X-ray powder diffraction pattern obtained using copper $K_\alpha$ radiation that comprises 2Θ values in degrees of about 2Θ values (i.e., reflections at 2Θ values) in degrees of about 5.0, 8.7, 10.1, 13.4, 15.1, 17.6, 20.3, 21.4, 22.2 and 23.3.

In a fourth aspect of the fifth compound embodiment, Anhydrous Form I is substantially pure.

A sixth compound embodiment is directed to Anhydrous Form II of

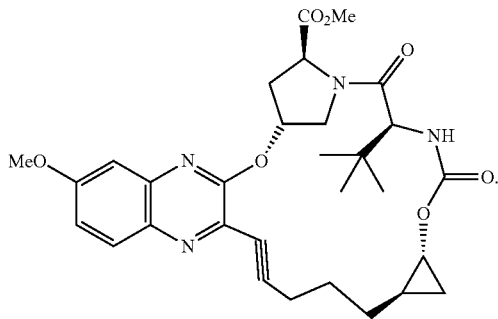

Figure 6:
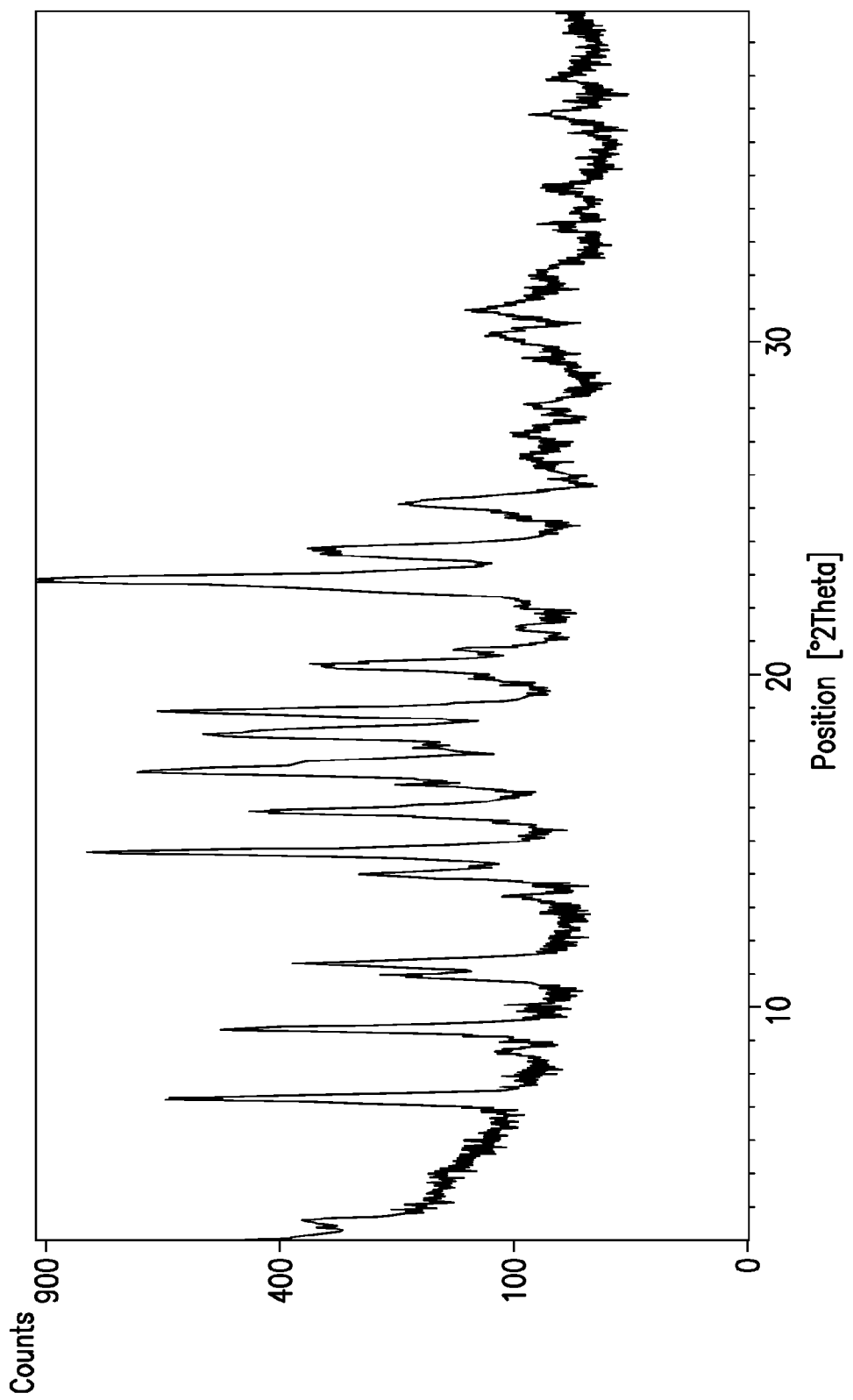
FIG. 6 provides a characteristic X-ray diffraction pattern for the crystalline macrocyclic ester anhydrous form II of Example 14B.

Anhydrous Form II is characterized by an X-ray powder diffraction pattern obtained using copper $K_\alpha$ radiation (i.e., the radiation source is a combination of Cu $K_{\alpha 1}$ and $K_{\alpha 2}$ radiation), which comprises three or more characteristic peaks. Characteristic peaks are illustrated in FIG. 6.

In a first aspect of the sixth compound embodiment, Anhydrous Form II is characterized by an X-ray powder diffraction pattern obtained using copper $K_\alpha$ radiation that comprises 2Θ values in degrees of about 2Θ values (i.e., reflections at 2Θ values) in degrees of about 14.7, 18.9, and 22.8.

In a second aspect of the sixth compound embodiment, Anhydrous Form II is characterized by an X-ray powder diffraction pattern obtained using copper $K_\alpha$ radiation that comprises 2Θ values in degrees of about 2Θ values (i.e., reflections at 2Θ values) in degrees of about 7.2, 9.3, 10.9, 11.3, 14.7, 18.9, 22.8, 23.8, and 25.1.

In a third aspect of the sixth compound embodiment, Anhydrous Form II is characterized by an X-ray powder diffraction pattern obtained using copper $K_\alpha$ radiation that comprises 2Θ values in degrees of about 2Θ values (i.e., reflections at 2Θ values) in degrees of about 7.2, 9.3, 11.3, 14.7, 18.9, and 22.8.

In a fourth aspect of the sixth compound embodiment, Anhydrous Form II is substantially pure.

A seventh compound embodiment is directed to a crystalline isopropyl alcohol solvate/hydrate (IPA solvate/hydrate) of

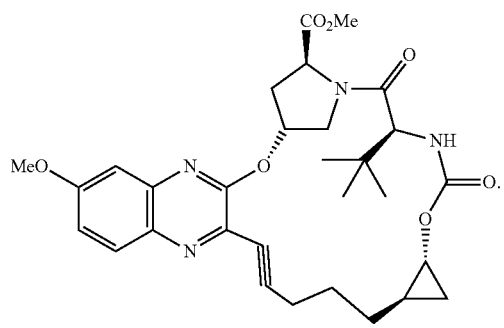

Figure 9:
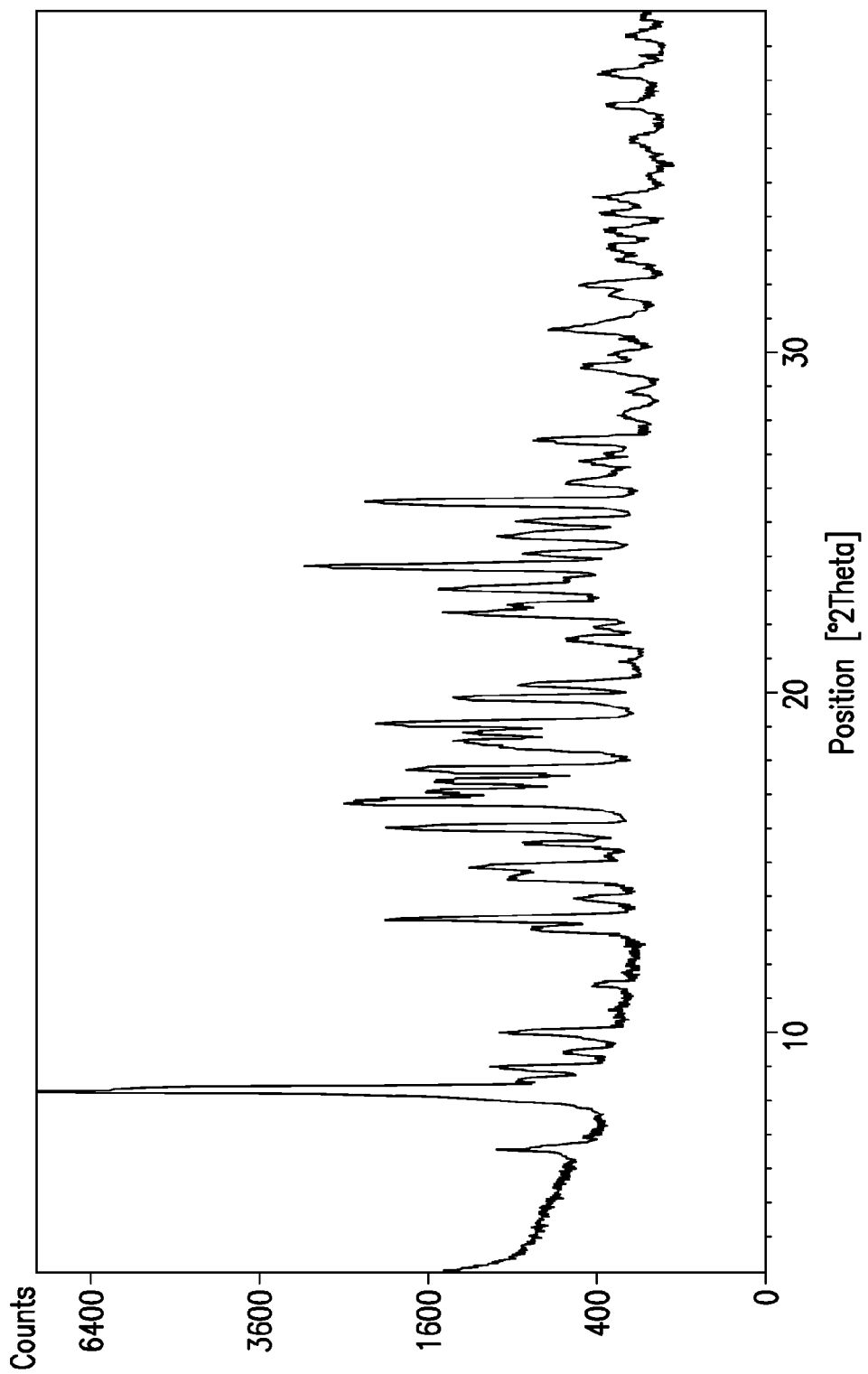
FIG. 9 provides a characteristic X-ray diffraction pattern of the crystalline IPA solvate/hydrate of Example 14C.

The IPA solvate/hydrate is characterized by an X-ray powder diffraction pattern obtained using copper $K_\alpha$ radiation (i.e., the radiation source is a combination of Cu $K_{\alpha 1}$ and $K_{\alpha 2}$ radiation), which comprises three or more characteristic peaks. Characteristic peaks are illustrated in FIG. 9.

In a first aspect of the seventh compound embodiment, the IPA solvate/hydrate is characterized by an X-ray powder diffraction pattern obtained using copper $K_\alpha$ radiation that comprises 2Θ values in degrees of about 2Θ values (i.e., reflections at 2Θ values) in degrees of about 8.4, 16.0, and 23.7.

In a second aspect of the seventh compound embodiment, the IPA solvate/hydrate is characterized by an X-ray powder diffraction pattern obtained using copper $K_\alpha$ radiation that comprises 2Θ values in degrees of about 2Θ values (i.e., reflections at 2Θ values) in degrees of about 8.4, 16.0, 17.7, 19.1, 23.7, and 25.5.

In a third aspect of the seventh compound embodiment, the IPA solvate/hydrate is characterized by an X-ray powder diffraction pattern obtained using copper $K_\alpha$ radiation that comprises 2Θ values in degrees of about 2Θ values (i.e., reflections at 2Θ values) in degrees of about 6.7, 8.4, 13.4, 14.9, 15.6, 16.0, 17.7, 19.1, 19.8, 23.7, and 25.5.

In a fourth aspect of the seventh compound embodiment, the IPA solvate/hydrate is substantially pure.

EXAMPLES

The examples provided below are intended to illustrate the invention and its practice. Unless otherwise provided in the claims, the examples are not to be construed as limitations on the scope or spirit of the invention.

Abbreviations $^{13}$C NMR Carbon-13 nuclear magnetic resonance spectroscopy
$^{1}$H NMR Proton nuclear magnetic resonance spectroscopy
AcOH Acetic acid
aq., aq Aqueous
BOC tert-Butoxycarbonyl
Br$_2$ Bromine
Bu Butyl, C$_4$H$_9$
CDCl$_3$ Deuterated chloroform
CDI Carbonyl diimidazole
CH$_2$Cl$_2$ Dichloromethane
Cu—I, CuI Copper (I) iodide
DAP 1,3-Diaminopropane
DBU 1,8-Diazabicyclo[5.4.0]undec-7-ene
DIPEA, DIE Diisopropyl ethyl amine (Hunig's base)
DMAc Dimethylacetamide
DMPU 1,3-Dimethyl-3,4,5,6-tetrahydro-2(1 H)-pyrimidinone
DMSO Dimethylsulfoxide
EDC 1-Ethyl-3-(3-dimethylaminopropyl)carbodiimide
eq Equivalents, stoichiometric equivalents
Et Ethyl, C$_2$H$_5$
EtOAc Ethyl acetate
g Grams
h Hours
H$_2$ Hydrogen gas, hydrogen gas atmosphere
H$_3$PO$_4$ Phosphoric acid
HATU 1-[Bis(dimethylamino)methylene]-1H-1,2,3-triazolo[4,5-b]pyridinium 3-oxide hexafluorophosphate
HCl Hydrochloric acid
HexLi Hexyl lithium
HPLC High performance liquid chromatography
IPA, i-PrOH Isopropyl alcohol
KF Karl Fischer titration
kg Kilogram
L Liter
LiNH$_2$ Lithium amide
M Molar
Me Methyl, CH$_3$
MeCN, CH$_3$CN Acetonitrile
MeMgBr Methylmagnesium bromide
MeMgCl Methylmagnesium chloride
MeOAc Methyl acetate
MeOH, CH$_3$OH Methanol, CH$_3$OH
MeSO$_3$H Methanesulfonic acid
MeTHF, 2-MeTHF 2-Methyl tetrahydrofuran
mg Milligram
MHz Megahertz
min Minutes
mL, ml milliliter
mM Millimolar
mm Millimeter
mmole millimole
Mol mole
MTBE Methyl tert-butyl ether
N Normal
N$_2$ Nitrogen gas, nitrogen gas atmosphere
Na$_2$CO$_3$ Sodium carbonate
Na$_2$S$_2$O$_3$ Sodium thiosulfate
NaCl Sodium chloride
NaOH Sodium hydroxide
NH$_4$Cl Ammonium chloride
nm Nanometer
nM Nanomolar
NMP N-Methyl-2-pyrrolidone
Pd/C Palladium on carbon
ppm Parts per million
psig Pounds per square inch [gauge],
1 Pascal=0.000145037738007 psig
pTSA p-Toluenesulfonic acid
Py Pyradine
RT, rt Room temperature or ambient temperature, approximately 25° C.
TBA tert-Butylamine
TEA Triethylamine
TFAA Trifluoroacetic anhydride
THF Tetrahydrofuran
UHP Urea hydrogen peroxide
V, v, vol Volume
v/v Volume per volume
w/w Weight per weight
wt % Percent by weight with respect to weight
x Refers to the number of times a process is iterated (e.g., "washed 3x"="washed three times")
μl Microliter
μm Micromillimeter, micron
μs Microsecond Example 1

Epoxide Opening

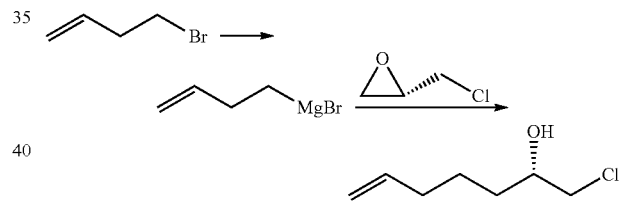

A 1-L 3-neck round-bottom flask equipped with an overhead stirrer, a condenser, an additional funnel, and a N$_2$ inlet was charged with 2-MeTHF (290 mL) and magnesium turnings (9.0 g, 0.37 mol), followed by iodine (0.45 g, 0.002 mol). The mixture was heated to 70° C. and agitated for 1.5 h. 4-Bromo-1-butene (47.5 g, 0.352 mol) was added dropwise over 1.5 h at 70° C. The mixture was aged 6 h at 70° C., and then cooled to RT.

A 1-L 3-neck round-bottom flask equipped with an overhead stirrer, an additional funnel, and a N$_2$ inlet was charged with (S)-(+)-epichlorohydrin (25.0 g, 0.27 mol), 2-MeTHF (150 mL) and Cu—I (2.56 g, 0.013 mol). The mixture was cooled to −60° C. The above solution of Grignard reagent was added via addition funnel over 1 h to 2 h while maintaining the reaction temperature <−50° C. The reaction mixture was aged for additional 1 h at <−50° C. Then, the reaction mixture was transferred to a solution of 5.6 M aq. NH$_4$Cl (400 mL) via cannula. The quenched mixture, at 10° C., was warmed to RT and stirred for additional 30 min. The layers were separated, and the organic phase was washed with 3.5 M aq. NH$_4$Cl (150 mL) followed by 10% (w/w) NaCl solution (100 mL). The organic phase was azeotropically distilled under vacuum to a volume of 150 mL and flushed with MeTHF (3×100 mL). The solution was assayed for 36.9 g of the desired product, 91.7% assay yield. The dried solution of chlorohydrin in MeTHF solution was used directly in the next reaction.

$^1$H NMR (500 MHz, CDCl$_3$) δ 5.80 (m, 1 H), 5.03 (d, J=17.1 Hz, 1 H), 4.98 (d, J =10.1 Hz, 1 H), 3.82 (m, 1 H), 3.64 (dd, J=11.1, 3.2 Hz, 1 H), 3.48 (dd, J=11.1, 7.1 Hz, 1 H), 2.18 (s, br, 1 H), 2.10 (m, 2 H), 1.59 (m, 1 H), 1.55 (m, 2 H), 1.48 (m, 1 H).

$^{13}$C NMR (125 MHz, CDCl$_3$) δ 138.5, 115.2, 71.5, 50.7, 33.8, 33.7, 25.0.

Example 2

Preparation of Cyclopropyl Amide

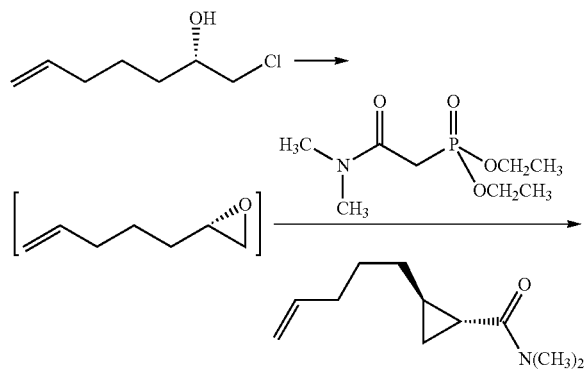

A 2-L 3-neck round-bottom flask equipped with a condenser, an overhead stirrer under N$_2$ was charged with 2-methyl-THF (600 mL, KF<300) and sodium tert-butoxide (61.9 g, 0.644 mol). The mixture was stirred for 30 min and then cooled to 0° C. to 5° C.

To a 2-MeTHF solution of chlorohydrin from Step 1 (36.9 g assay, 0.248 mol, KF=220) from Example 1 was added diethyl[2-(dimethylamino)-2-oxoethyl] phosphonate (80.2 g, 86 wt %, 0.309 mol). This mixed solution (~230 mL) was transferred via cannula to the above sodium tert-butoxide solution over 10 min with the temperature rising to 18° C. The reaction solution was heated to 78° C. and aged for 20 h. The reaction solution was cooled to RT (20° C.), and water (375 mL) was added dropwise, while the internal temperature was maintained at <25° C. with external cooling. The separated organic phase was washed with 10% w/w NaCl solution (3×100 mL). The organic phase was then azeotropically distilled under vacuum at a pot temperature of 23° C. to 28° C. to a volume of 200 mL. The organic phase was assayed (HPLC) for 37.0 g of cyclopropyl amide, 82% assay yield. The dried solution of cyclopropyl amide in MeTHF was directly used in the subsequent reaction without further purification. For epoxide intermediate:

$^1$H NMR (500 MHz, CDCl$_3$) δ 5.82 (m, 1 H), 5.04 (d, J=17.3 Hz, 1 H), 4.98 (d, J =10.2 Hz, 1 H), 2.93 (m, 1 H), 2.76 (m, 1 H), 2.48 (m, 1 H), 2.13 (m, 2 H), 1.57 (m, 4 H).

$^{13}$C NMR (125 MHz, CDCl$_3$) δ 138.5, 115.0, 52.4, 47.3, 33.6, 32.1, 25.4.

For N,N-dimethyl amide product:

$^1$H NMR (500 MHz, d$_4$-MeOH) δ 5.81 (m, 1 H), 5.00 (m, 1 H), 4.93 (m, 1 H), 3.20 (s, 3 H), 2.94 (s, 3 H), 2.09 (m, 2 H), 1.67 (m, 1 H), 1.52 (m, 2 H), 1.37 (m, 1 H), 1.25 (m, 1 H), 1.07 (m, 1 H), 0.67 (m, 1 H).

$^{13}$C NMR (125 MHz, d$_4$-MeOH) δ 175.8, 140.0, 115.2, 38.0, 36.4, 34.6, 33.7, 29.9, 23.2, 19.7, 15.5.

Example 3

Methyl Grignard Addition

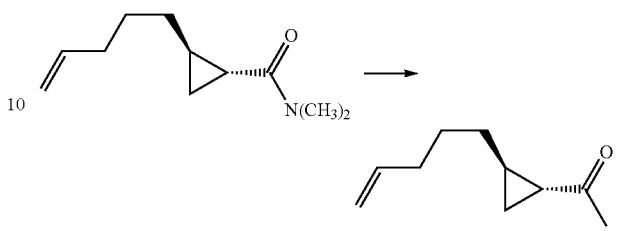

A 500-mL round-bottom flask under N$_2$ was charged with 3 M MeMgCl in THF (135 mL, 0.404 mol). The solution was heated to 60° C. The dried solution of cyclopropyl amide in 2-MeTHF solution from Example 2 (36.6 g assay, 0.202 mol, ~200 mL, KF<500) was added dropwise to the Grignard solution over 2.5 h. After addition, the reaction solution was aged at 60° C. for additional 1 h. The reaction was quenched to a solution of 5.7 M aq. NH$_4$Cl (460 mL) and hexanes (425 mL), while the internal temperature was maintained between 20° C. to 25° C. with external cooling. The quenched mixture was stirred at RT for additional 1 h. The separated organic phase was washed with 1 N HCl (100 mL) followed by 10% w/w NaCl solution (100 mL). The organic phase was azeotropically distilled under vacuum at a volume of ~60 mL, while maintaining the internal temperature at <15° C. 27.5 g of assayed cyclopropyl methyl ketone, 90% assay yield.

$^1$H NMR (500 MHz, CDCl$_3$) δ 5.78 (m, 1 H), 5.00 (d, J=17.1 Hz, 1 H), 4.94 (d, J =9.92 Hz, 1 H), 2.21 (s, 3 H), 2.06 (m, 2 H), 1.69 (m, 1 H), 1.48 (m, 2 H), 1.38 (m, 1 H), 1.34 (m, 2 H), 1.32 (m, 1 H), 1.23 (m, 1 H).

$^{13}$C NMR (125 MHz, CDCl$_3$) δ 208.4, 138.7, 114.8, 33.5, 32.8, 30.4, 29.4, 28.6, 25.9, 18.2.

Example 4

Bromination, Method A

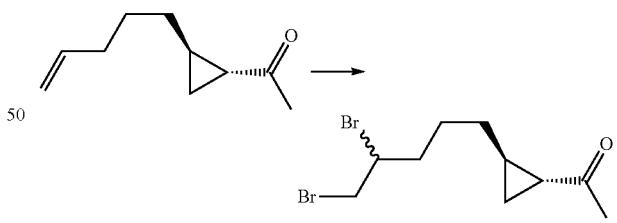

To a solution of methyl ketone in hexane from Example 3 (10.0 g assay, 65.7 mmol, containing ~1 vol hexanes, KF<200 ppm) was added CH$_2$Cl$_2$ (100 mL). The solution was cooled to −45° C. to −50° C. Br$_2$ (10.50 g, neat, 65.7 mmol) was added dropwise over 1 h via syringe pump, while maintaining the temperature between −45° C. to −50° C. After additional 20 min aging, a second portion of Br$_2$ (3.15 g, 19.8 mmol) was added dropwise between −45° C. to −50° C. over 20 min. The reaction mixture was agitated for additional 20 min. DIPEA (2.12 g, 16.4 mmol) was added dropwise over 15 min, maintaining the internal temperature between −45° C. to −50° C. The reaction mixture was then inverse-quenched to a solution of 10% Na$_2$S$_2$O$_3$ in 5% NaCl aq. (50 mL). The reaction mixture was pH adjusted to 4-6 with 1.0 N HCl (~10 mL to 20 mL). After stirring for 20 min, the organic phase (the bottom layer) was separated and washed with water (30 mL). The organic phase was azeotropically solvent-switched to EtOAc (160 mL) below 15° C. until the KF of the mixture <500 ppm. Typical assay yield is 85% to 89%. The dried solution of bromo ketone in EtOAc was directly used in the next reaction without further purification.

The bromide product is a mixture of diastereomers.

$^1$H NMR (500 MHz, CDCl$_3$) δ 4.16 (m, 1 H), 3.85 (m, 1 H), 3.62 (m, 1 H), 2.23 and 2.20 (s, 3 H), 2.18 (m, 1 H), 1.81 (m, 1 H), 1.73 (m, 2 H), 1.53 (m, 1 H), 1.38 (m, 3 H), 1.26 (m, 1 H), 0.77 (m, 1 H).

$^{13}$C NMR (125 MHz, CDCl$_3$) δ 208.17, 208.15, 52.82, 52.79, 36.30, 36.27, 35.71, 35.67, 32.50, 32.47, 30.50, 30.45, 29.24, 29.12, 26.61, 26.53, 25.48, 25.41, 18.16, 18.05.

Example 5

Bromination, Method B

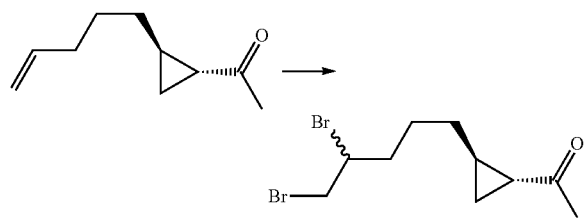

To a solution of methyl ketone in hexane from Example 3 (10 g assay, 65.7 mmol, ~50 wt %) was added MeCN (30 mL) followed by pyridine (2.6 g, 32.85 mmol). The batch was cooled to −5° C. to 5° C. A solution of pyridinium tribromide (25.2 g, 92 mmol) in MeCN (50 mL) was added dropwise over several hours, while maintaining the batch temperature between −5° C. and 5° C. After aging the reaction slurry for additional 30 min, a solution of 10% Na$_2$S$_2$O$_3$ in 5% NaCl aq. (30 mL) was slowly charged. The batch was agitated at RT for at least 30 min. EtOAc (60 mL) was charged to the separated organic layer, followed by 0.5N HCl (40 mL). The organic phase was then washed with 15% aq. NaCl (20 mL). The organic phase was aezotropically dried and solvent-switched to EtOAc at a final volume of ~80 mL under vacuum. Typical assay yield is 91 to 93%. The crude stream of bromo ketone may be used directly in the subsequent step without further purification.

Example 6

Baeyer-Villiger Oxidation

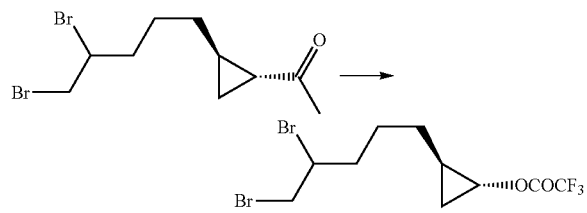

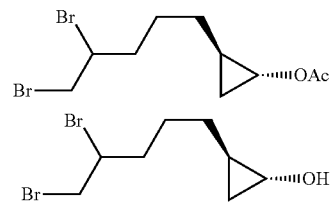

The solution of di-Br ketone (20.0 g assay, 64.1 mmol) in EtOAc (160 mL, KF<500 ppm) from Example 4 was cooled to 0° C. UHP (24.1 g, 256.4 mmol) was added in portions. TFAA (55.2 g, 262.8 mmol) was then added dropwise under N$_2$ over 3 h, while the internal temperature was maintained between 0° C. to 3° C. The resulting mixture stirred overnight at 0° C. (~16 h) until HPLC showed that conversion was greater than >95%. The reaction mixture was pH adjusted to 7-8 by addition of 20% Na$_2$CO$_3$ (~140 mL, 265 mmol), while the internal temperature was maintained below 5° C. with external cooling. The organic phase was separated. The aqueous layer was extracted with EtOAc (100 mL). The combined organic phase was washed with 10% Na$_2$S$_2$O$_3$ in 5% NaCl aq. (w/w, 60 mL) followed by 10% NaCl aq. solution (60 mL). The organic layer was azeotropically solvent-switched to hexanes (100 mL) until the content of EtOAc is <1% (by $^1$H NMR assay) and KF<500 ppm. The slurry was agitated at 20° C. for additional 1 h; the solid was removed through filtration. The wet cake was washed with hexanes (3×20 mL). The combined filtrate was concentrated to a volume of ~50 mL to 60 mL (contained ~1 vol of hexane). Typical assay yield is 92%-95% (the combined yield). The concentrated crude process stream was used directly for the next reaction. The bromide acetate product is a mixture of diastereomers.

$^1$H NMR (500 MHz, CDCl$_3$) δ 4.18 (m, 1 H), 3.87 (m, 1 H), 3.84 (m, 1 H), 3.65 (m, 1 H), 2.19 (m, 1 H), 2.03 (s, 3 H), 1.83 (m, 1 H), 1.73 (m, 1 H), 1.58 (m, 1 H), 1.36 (m, 1 H), 1.29 (m, 1 H), 1.04 (m, 1 H), 0.86 (m, 1 H), 0.57 (m, 1 H).

$^{13}$C NMR (125 MHz, CDCl$_3$) δ 171.9, 54.53, 54.47, 53.0, 36.49, 36.46, 35.87, 35.82, 30.8, 30.7, 26.20, 26.12, 21.14, 18.40, 18.37, 12.21, 12.12.

The bromide alcohol product is a mixture of diastereomers.

$^1$H NMR (500 MHz, CDCl$_3$) δ 4.39 (m, 1 H), 3.89 (m, 1 H), 3.86 (m, 1 H), 3.65 (m, 1 H), 3.24 (m, 1 H), 2.19 (m, 1 H), 1.84 (m, 2 H), 1.69 (m, 1 H), 1.54 (m, 1 H), 1.30 (m, 1 H), 1.18 (m, 1 H), 0.95 (m, 1 H), 0.74 (m, 1 H), 0.36 (m, 1 H).

$^{13}$C NMR (125 MHz, CDCl$_3$) δ 53.11, 53.06, 52.9, 52.8, 36.5, 35.9, 35.8, 31.1, 31.0, 26.44, 26.38, 20.81, 20.78, 14.8, 14.7.

Example 7

De-Bromination, Method A

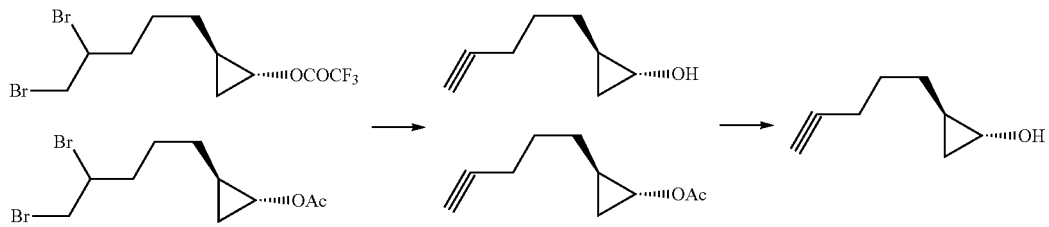

A 1-L 3-neck round-bottom flask equipped with an overhead stirrer, an additional funnel, and a $N_2$ inlet was charged with DAP (151 mL). The solution was cooled to 0° C. HexLi (2.3 M, 188 mL, 433 mmol) was charged dropwise over 1 h, maintaining the temperature below 5° C. After the addition, the reaction mixture was stirred at 0° C. for additional 30 min. A solution of bis-Br esters (total 72.2 mmol assay, ~50 mL of ~50% v/v solution in hexane) prepared from Example 6 was added to the above slurry mixture dropwise over 1 h, while maintaining internal temperature at 0° C.±2° C. The reaction mixture was stirred at 0° C. for additional 0.5 h to 1 h.

A 1-L 3-neck round-bottom flask equipped with an overhead stirrer was charged with 10% aq. $NH_4Cl$ (240 mL) and MTBE (240 mL). The solution was cooled to 0° C. Then, the debrominated reaction mixture was transferred to the cold solution of $NH_4Cl$/MTBE through flexible tubing under partial vacuum with a good mixing over 20 min, while the internal temperature was maintained below 5° C. The debromination reaction flask and tubing were rinsed/washed with a cold solution of $NH_4Cl$ (10%, 24 mL)/MTBE (24 mL). The resulting quenched mixture was stirred at 5° C. for additional 30 min until the solid was dissolved. The organic phase was retained, and the aqueous layer was further extracted with MTBE (120 mL). The combined organic phase was washed with 10% $NH_4Cl$ aq. (120 mL), followed by 10% NaCl (120 mL). The organic phase was concentrated and solvent-switched into MeOH to a volume of ~60 mL at <15° C. under reduced pressure. The reaction solution was cooled to 0° C. NaOH aq. solution (1 N, 50 mL, 50 mmol) was added dropwise, maintaining the internal temperature at 0° C. to 5° C. The reaction mixture was stirred at 0° C. for additional 0.5 h to 1 h. 10% $NH_4Cl$ aq. solution (120 mL) and MTBE (120 mL) were added. The two phases were separated. The separated aqueous phase was back-extracted with MTBE (120 mL). The combined organic phase was washed with 10% NaCl (40 mL). The organic phase was azeotropically solvent-switched to EtOAc to a final volume of ~30 mL until KF<500 ppm. Typical assay yield is 80% to 84%. The crude process stream was used directly for the next reaction.

$^1$H NMR (500 MHz, $CDCl_3$) δ 3.20 (m, 1 H), 2.31 (s, br, 1 H), 2.21 (m, 2 H), 1.92 (t, J=2.6 Hz, 1 H), 1.60 (m, 2 H), 1.33 (m, 1 H), 1.21 (m, 1 H), 0.89 (m, 1 H), 0.68 (m, 1 H), 0.32 (m, 1 H).

$^{13}$C NMR (125 MHz, $CDCl_3$) δ 84.7, 68.6, 52.7, 30.7, 28.0, 20.4, 18.2, 14.5.

Example 8

De-Bromination, Method B

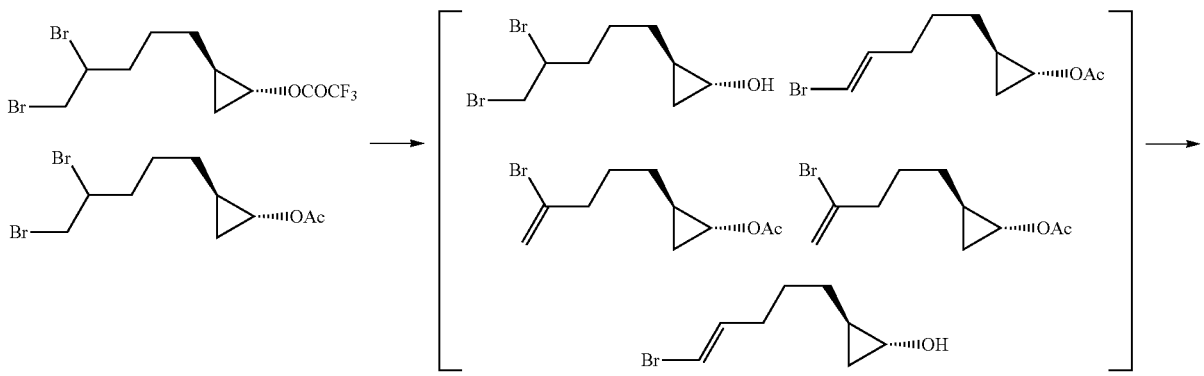

A 250-mL 3-neck round-bottom flask equipped with an overhead stirrer and a N$_2$ inlet was charged with DAP (120 mL). Then, LiNH$_2$ (6.83 g), 297 mmol) was charged in 2 portions (slightly exothermic). The resulting suspension was stirred at 22° C. to 25° C. for 1 h to 2 h, and then the suspension was cooled to 0° C. A solution of bis-Br esters (total 45.7 mmol assay, ~40 ml, of ~50% v/v solution in THF, KF<500 ppm) prepared from the Example 6 was added to the above slurry mixture dropwise over 1 h, while maintaining batch internal temperature at 0° C.±3° C. The reaction mixture was stirred at 0° C. for additional 2 h to 3 h. The reaction mixture was warmed to 22° C. to 25° C. over 2 h to 3 h and aged at 22° C. to 25° C. for additional 5 h to 6 h until molar conversion was greater than 95%. Then, the reaction mixture was cooled to 0° C. and quenched to a cold solution (0° C.) of 15% aq. NH$_4$Cl (150 mL) and MTBE (150 mL) through flexible tubing under partial vacuum with a good mixing over 0.5 h, while the internal temperature was maintained below 5° C. The debromination reaction flask and tubing were rinsed/washed with the cold solution of NH$_4$Cl (15%, 24 mL)/MTBE (24 mL). Then, the resulting quenched mixture was stirred at 20° C. for additional 30 min until the entire solid was dissolved. The organic phase was retained, and the aqueous layer was further extracted with MTBE (75 mL). The combined organic phase was washed with 15% NH$_4$Cl aq. (75 mL), followed by 10% NaCl (75 mL). The organic phase was azeotropically solvent-switched to EtOAc to a final volume of ~30 mL until KF<500 ppm. Typical assay yield is 72% over 2 steps (Baeyer-Villiger oxidation & debromination). The crude process stream may be used directly for the next reaction.

Example 9

De-Bromination, Method C

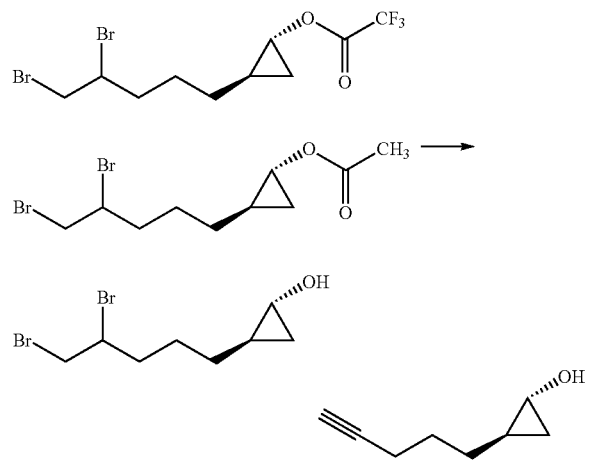

n-BuLi (2.5 M in hexanes, 25.8 mL, 64.61 mmol) was added dropwise to a solution of 1,3-diaminopropane (2.52 g, 33.97 mmol) in 2-MeTHF (36 mL) at −25° C. to −15° C. under N$_2$, while maintaining the batch temperature below −15° C. The resulting slurry was agitated at −15° C.±5° C. for 1 h, warmed to between 20° C. to 25° C. over 2 h and agitated for additional 1 h. The batch was then cooled to between 0° C. to 25° C. A solution of bis-bromides prepared from the Example 6 (9.23 mmol assay of combined) was added dropwise over 1-5 h, while maintaining the batch temperature around 0° C. to 25° C. DMPU (4.73 g, 36.92 mmol) was added, and the batch was agitated at 20° C. to 25° C. for several hours. Water (40 mL) was added slowly, while maintaining the internal temperature between 15° C. to 30° C. The batch was agitated at RT for additional 2 h to 4 h, and filtered through SOLKA-FLOC® (powdered cellulose, International Fiber Corporation, North Tonawanda, N.Y.). The wet cake was washed with 2-MeTHF/hexanes (1:1 v/v, 9 mL). The organic phase was separated, and the aqueous layer was extracted with 2-MeTHF/hexanes (1:1 v/v, 18 mL). The combined organic phase was washed with 20% NH$_4$Cl (15 mL) followed by water (2×15 mL). The organic phase was azeotropically dried and solvent-switched to 2-MeTHF at a final volume of ~5 mL. Typical yield ~95%. The concentrated crude process stream may be used directly for the subsequent step without further purification.

Example 10

Carbamate Formation, Method A

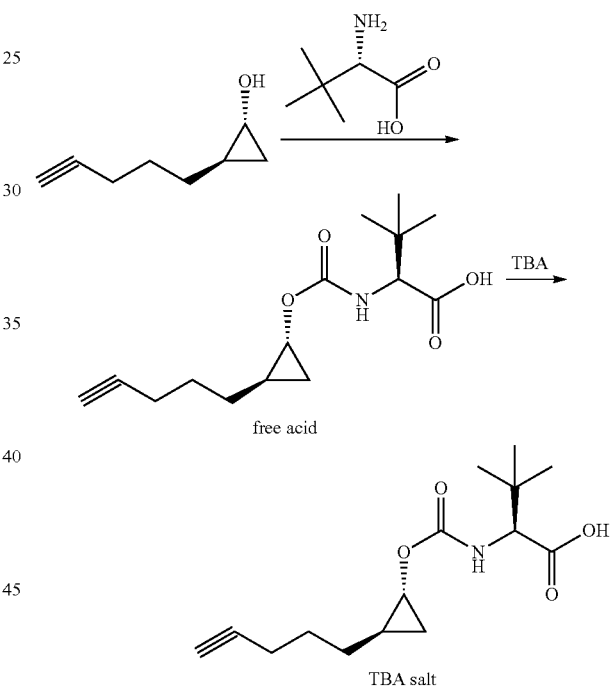

A slurry of CDI (7.6 g, 44.3 mmol) in EtOAc (75 mL) was cooled to 0° C. A solution of alkyne alcohol (5.0 g active assay, 40.3 mmol) in EtOAc (7.5 mL) from Example 7 was added slowly in about 1 h, while maintaining the temperature at 0° C. The reaction mixture was stirred at 0° C. for additional 1 h. Water (40 mL) was added slowly at 0° C., and resulting mixture was stirred at 0° C. for 1 h. The organic phase was separated. The organic phase was azeotropically dried to a KF<250 ppm with EtOAc in vacuum at below 20° C. (internal temperature). The solvent was then azeotropically switched to NMP at a final volume of ~95 mL. L-tert-leucine (6.3 g, 48.4 mmol) and 2-hydroxypyridine N-oxide (1.79 g, 16.1 mmol) were added to the above anhydrous solution. The reaction mixture was heated up to between 60° C. to 65° C. and stirred for 10 h to 15 h. The reaction mixture was cooled to 0° C., and water (75 mL) was slowly added. 5 N HCl solution (30 mL) was added slowly to adjust pH to ~2 by pH meter. The two phases were separated. The aqueous phase was back-extracted with MTBE (75 mL) twice. The organic phase was washed with water (75 mL) and then azeotropically distilled at a final volume of ~95 mL. IPA (16 mL, 3.2 v) was added, and the solution was heated to 40° C. At 40° C., TBA (1.85 mL, 17.5 mmol) was slowly added over about 30 min. The slurry was stirred at 40° C. for about 30 min to form a seed bed. Additional TBA (3.69 mL, 34.9 mmol) was slowly added at 40° C. in about 1 h. After aging at 40° C. for additional 1 h, the slurry was slowly cooled to 20° C. and aged for 1 h. The slurry was further cooled to 0° C. and stirred for 1 h before filtration. The wet cake washed with 5% IPA/MTBE solution (2×30 mL, pre-cooled to 0° C.). The wet cake was dried under vacuum at 40° C. with N₂ sweep to give 12.4 g of TBA salt.

¹H NMR (400 MHz, CDCl₃) δ 8.19 (s, br, 3 H), 6.04 (d, J=8.4 Hz, 1 H), 3.60 (m, 1 H), 3.45 (d, J=8.4 Hz, 1 H), 2.72 (t, J=2.7 Hz, 1 H), 2.18 (td, J=7.1, 2.7 Hz, 2 H), 1.54 (m, 2 H), 1.26 (m, 2 H), 1.22 (s, 9 H), 0.89 (m, 1 H), 0.88 (s, 9 H), 0.76 (m, 1 H), 0.44 (m, 1 H).

¹³C NMR (100 MHz, CDCl₃) δ 172.9, 156.1, 84.4, 71.2, 64.2, 53.5, 50.0, 34.0, 29.7, 27.7, 27.18, 27.15, 17.6, 17.3, 11.3.

An X-ray powder diffraction pattern was generated to characterize the molecular structure of the TBA salt of (S)-3,3-dimethyl-2-(((1R,2R)-2-(pent-4-ynyl)cyclopropoxy) carbonylamino) butanoic acid. The pattern was generated on a Philips Analytical X'Pert PRO X-ray Diffraction System with PW3040/60 console, using a PW3373/00 ceramic Cu LEF X-ray tube K-Alpha radiation as the source. The pattern, shown in FIG. 1, exhibited characteristic reflections corresponding to d-spacings as follows.

| Position [° 2 θ] | d-spacing [Å (Å = 0.1 nm)] |
| --- | --- |
| 8.8 | 10.1 |
| 20.1 | 4.4 |
| 11.7 | 7.6 |
| 27.7 | 3.2 |
| 14.8 | 6.0 |
| 23.7 | 3.8 |
| 29.0 | 3.1 |
| 31.8 | 2.8 |
| 31.0 | 2.9 |

Example 11

Carbamate Formation, Method B

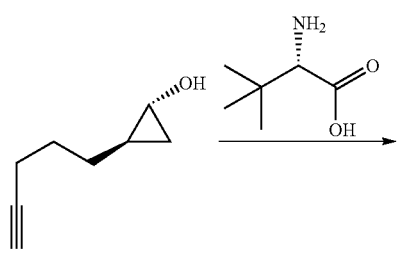

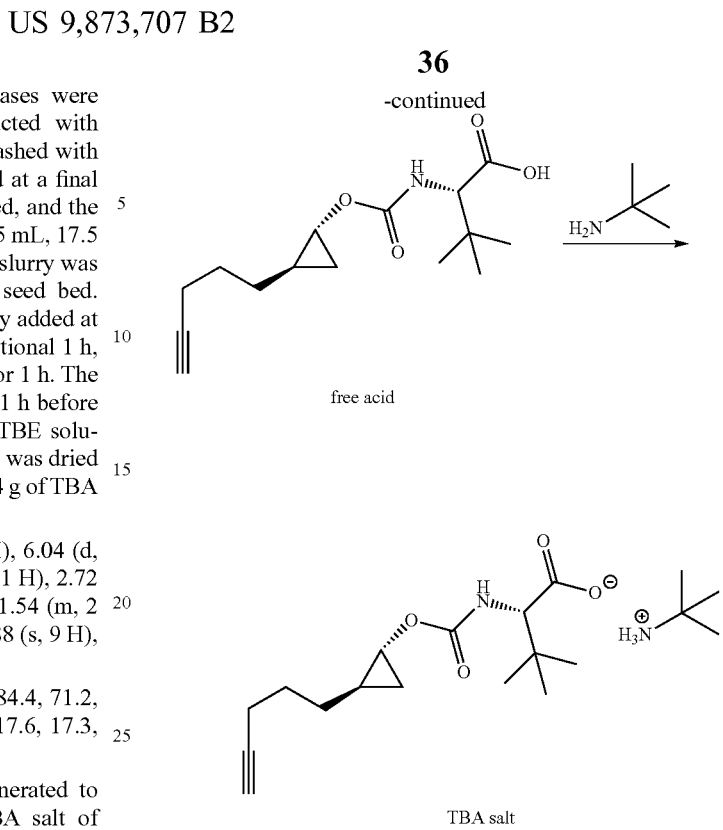

free acid

TBA salt

A solution of alkyne alcohol (3.2 g assay, 25.85 mmol) in 2-MeTHF from Example 7 was added to a mixture of CDI (5.62 g, 33.61 mmol) in 2-MeTHF (32 mL) at 0° C.±5° C. over 2 h to 5 h. The reaction solution was agitated for additional 1 h to 2 h. Water (16 mL) was added dropwise, while maintaining the internal temperature at 0° C. to 5° C. The reaction solution was then agitated at 0° C. to 5° C. for additional 1 h to 2 h. Heptane (38 mL) was added. The organic phase was separated, and the aqueous layer was extracted with 2-MeTHF/heptane (1:1, 10 mL). The combined organic phase was washed with water (16 mL). The organic phase was azeotropically dried and solvent-switched to 2-MeTHF at a final volume of ~10 mL. NMP (56 mL) was added, followed by tert-L-leucine (4.19 g, 31.02 mmol) and 2-hydroxypyridine N-oxide (1.17 g, 10.34 mmol). The reaction mixture was agitated between 60° C. to 65° C. for 10 h to 18 h. MTBE (48 mL) and water (48 mL) were added at RT. The batch was pH adjusted with 5N HCl to pH=2.0-2.5. The organic phase was separated, and the aqueous layer was extracted with MTBE (48 mL). The combined organic phase was washed with water (2×32 mL). The organic phase was extracted with NaOH aq. (1 N, 40 mL). The separated aqueous phase was washed with MTBE (2×32 mL). MTBE (50 mL) was added, and the batch was pH adjusted to pH=2.0-2.5. The organic phase was washed with water (16 mL). The organic phase was azeotropically dried under reduced pressure at a final volume of ~110 mL containing ~1 wt % water. A solution of TBA (2.48 g, 33.61 mmol) in MTBE (3 mL) was added dropwise at 40° C.±5° C. After ~35% of the above TBA solution was added, the batch was seeded. The remaining TBA solution was added dropwise over 2 h to 4 h. After aging at 40° C.±5° C. for additional 1 h to 2 h, the batch was cooled to RT and filtered. The wet cake was washed MTBE (3×30 mL) and dried in a vacuum oven at 30° C. to 35° C. with N₂ sweep, which afforded the TBA salt. Typical yield: 76-81%.

Example 12

Preparation of (2S,4R)-4-(3-chloro-7-methoxyquinoxalin-2-yloxv)-2-(methoxycarbonyl)pyrrolidinium methanesulfonate

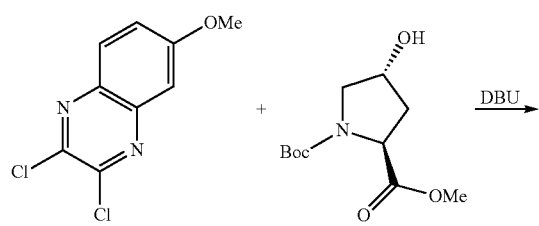

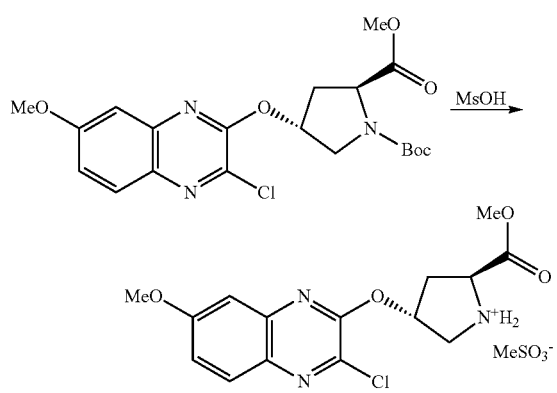

To a slurry of 2,3-dichloroquinoxaline (100 g, 0.437 mol) and N-Boc-4-trans-hydroxy-L-proline methyl ester (118 g, 0.48 mol) in DMAc (500 ml, KF<150) at RT, DBU (86 g, 0.568 mol) was added. The slurry was agitated at 40° C. to 45° C. for ~35 h. The batch was then cooled to 15° C. EtOAc (1.2 L) followed by citric acid (10%, 504 mL, 162 mmol) was added while the internal temperature was maintained at <25° C. The organic phase was washed with a solution of 10% citric acid (200 mL) and water (200 mL) followed by water (2×400 mL). The organic phase was azeotropically dried and solvent-switched to MeCN at a final volume of ~880 mL. MeSO$_3$H (36 mL, 0.555 mol) was added, and the reaction mixture was aged at 40° C. for ~16 h. To the reaction slurry, MTBE (1.05 L) was added dropwise over 2 h at 35° C. Then, the batch was further cooled to 0° C. to 5° C. and aged for 2 h to 3 h before filtration. The wet cake was displacement washed with 30% MeCN in MTBE (2×600 mL) and vacuum-oven dried at 40° C. to give the product.

$^1$H NMR (400 MHz, d$_6$-DMSO) δ 9.74 (s, br, 2 H), 7.86 (d, J=9.2 Hz, 1 H), 7.34 (dd, J=9.2, 2.8 Hz, 1 H), 7.26 (d, J=2.8 Hz, 1 H), 5.77 (m 1 H), 4.69 (dd, J=10.6, 7.6 Hz, 1 H), 3.92 (s, 3 H), 3.89 (dd, J=13.2, 5.2 Hz, 1 H), 3.81 (s, 3 H), 3.63 (m, 1 H), 2.71 (m, 1 H), 2.60 (m, 1 H), 2.35 (s, 3 H).

$^{13}$C NMR (100 MHz, d$_6$-DMSO) δ 168.3, 161.0, 151.8, 140.4, 135.4, 133.3, 128.6, 119.8, 106.0, 75.6, 58.0, 56.0, 53.2, 50.5, 39.6, 33.9.

HPLC conditions: Hypersil Gold PFP column, 150×4.6 mm, 3.0 μm; Column temperature of 40° C.; Flow rate of 1.8 mL/min; and Wavelength of 215 nm.

| Gradiant: | | |
|---|---|---|
| min | CH$_3$CN | 0.1% H$_3$PO$_4$ |
| 0 | 25 | 75 |
| 12 | 70 | 30 |
| 12.1 | 25 | 75 |
| 14 | 25 | 75 |

| Retention times: | min. |
|---|---|
| Dichloroquinoxaline | 7.8 |
| Proline quinoxaline | 9.8 |
| De-BOC quinoxaline | 3.6 |

Example 13

Preparation of (2S,4R)-4-(3-chloro-7-methoxyquinoxalin-2-yloxy)-2-(methoxycarbonyl)pyrrolidinium methanesulfonate

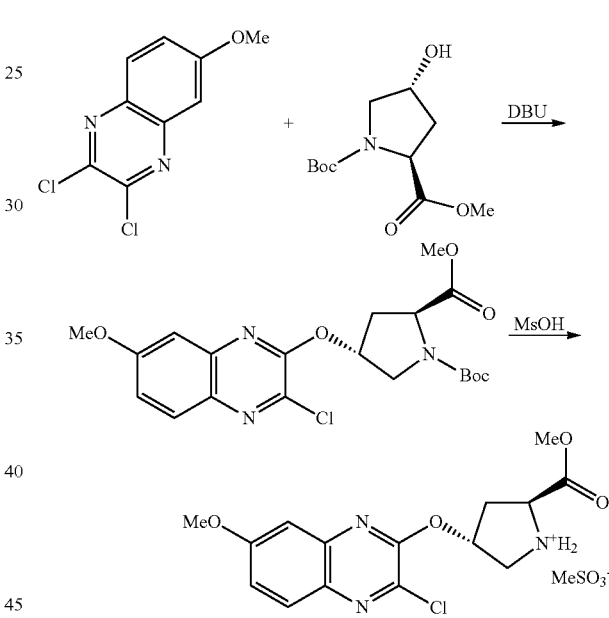

To a slurry of 2,3-dichloroquinoxaline (20 g, 0.087 mol) and N-Boc-4-trans-hydroxy-L-proline methyl ester (23.6 g, 0.096 mol) in DMAc (100 ml) at RT, DBU (17 mL, 0.114 mol) was added. The slurry was agitated at 50° C. for ~40 h. The batch was then cooled to 15° C. EtOAc (240 mL) followed by citric acid (10%, 97 mL) was added while the internal temperature was maintained at <25° C. The organic phase was washed with a solution of 10% citric acid (40 mL) and water (40 mL) followed by water (2×80 mL). The organic phase was azeotropically dried and solvent-switched to MeCN at a final volume of ~175 mL. MeSO$_3$H (7.2 mL, 0.111 mol) was added, and the reaction mixture was aged at 56° C. to 60° C. for 1 h to 3 h. The batch was seeded with 100 mg of methanesulfonate salt product seeds and aged for additional 7 h. To the reaction slurry, MTBE (120 mL) was added dropwise over 3 h at 55° C. Then, the batch was aged for 2 h, cooled to 0° C. to 5° C., and aged for 2 h before filtration. The wet cake was displacement washed with 30% MeCN in MTBE (3×120 mL) and vacuum oven-dried at 40° C. with N$_2$ sweep to give the product.

An X-ray powder diffraction pattern was generated to characterize the molecular structure of the methanesulfonate salt of (2S,4R)-4-(3-chloro-7-methoxyquinoxalin-2-yloxy)-2-(methoxycarbonyl)pyrrolidine. Powder X-ray Diffraction data were acquired on a Panalytical X-pert Pro PW3040 System configured in the Bragg-Brentano configuration and equipped with a Cu radiation source with monochromatization to Kα achieved using a Nickel filter. A fixed slit optical configuration was employed for data acquisition. Data were acquired between 2° and 40° 2θ. Samples were prepared by gently pressing powdered sample onto a shallow cavity zero background silicon holder. The pattern, shown in FIG. 2, exhibited characteristic reflections corresponding to d-spacings as follows.

| Position [° 2 θ] | d-spacing [Å (Å = 0.1 nm)] |
| --- | --- |
| 9.2 | 9.6 |
| 9.7 | 9.1 |
| 10.3 | 8.6 |
| 13.7 | 6.5 |
| 15.0 | 5.9 |
| 17.1 | 5.2 |
| 17.9 | 5.0 |
| 18.5 | 4.8 |
| 20.9 | 4.2 |

Example 14

Preparation of (S)-2-(((1R,2R)-2-(5-(6-methoxy-3-((3R,5S)-5-(methoxycarbonyl)pyrrolidin-3-yloxy)quinoxalin-2-yl)pent-4-ynyl)cyclopropoxy)carbonylamino)-3,3-dimethylbutanoic acid and alkene macrocyclic ester

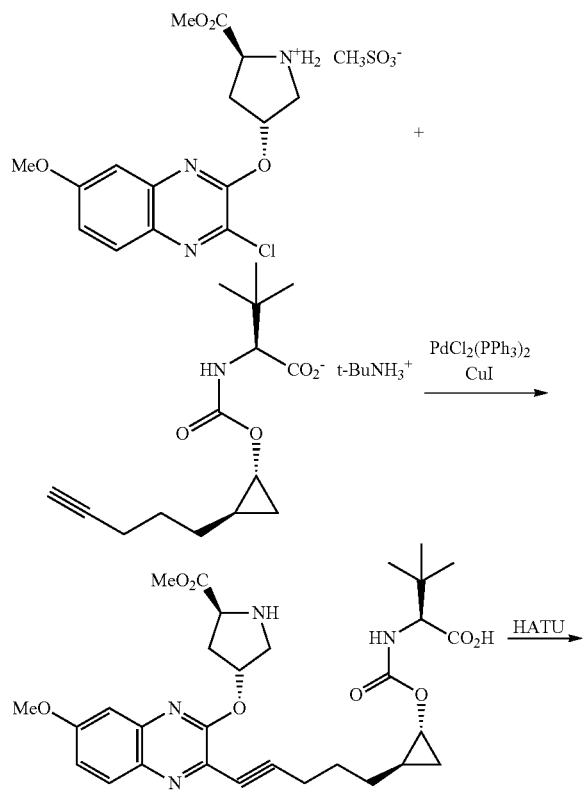

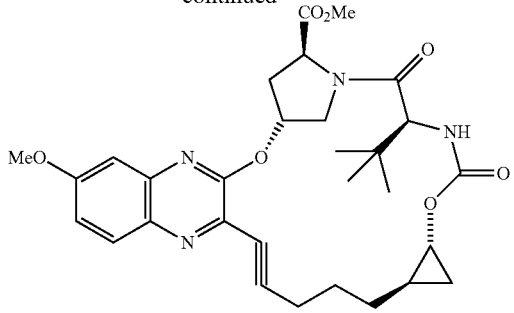

To a 3-neck flask were added CuI (0.219 g, 1.152 mmol), chloroquinoxaline MsOH salt from Example 12 (50 g, 115 mmol), alkyne acid TBA salt from Example 10 (49.3 g, 121 mmol), and bis(triphenylphosphine)palladium(II) dichloride (0.404 g, 0.573 mmol). The flask was vacuumed degassed with $N_2$. MeOH (500 ml) was added, and the reaction mixture was vacuum degassed again with $N_2$. TEA (32.1 ml, 230 mmol) was added. The reaction solution was aged at 35° C. for 3 h to 5 h. The batch was then concentrated to a volume of ~100 mL in vacuum. THF (250 mL) and EtOAc (250 mL) were added. The reaction mixture was cooled to below 5° C. HCl solution (1 N, ~180 mL) was added slowly at below 5° C. until the reaction solution was pH adjusted to ~2. NaCl aq. solution (10%, 350 mL) was added. The separated aqueous phase was back-extracted with a solution of THF (250 mL) and EtOAc (250 mL). The combined organic phase was washed with 10% NaCl aq. solution (500 mL). The organic phase was azeotropically concentrated in vacuum with THF at below 20° C. until the KF of the solution was less than 500 ppm. Then, the reaction solvent was switched to DMAc (650 mL) in vacuum at below 20° C.

A solution of HATU (55.1 g, 145 mmol) in DMAc (650 mL) at RT was vacuumed degassed with $N_2$. The solution was then cooled to 0° C., and DIPEA (58.5 mL, 335 mmol) was added dropwise at below 0° C. to 5° C. Then, the above solution of alkyne quinoxaline acid (65 g assay, 112 mmol) in DMAc was added dropwise over 10 h, while maintaining the internal temperature at 0° C. After addition, the batch was agitated at 0° C. for additional 2 h. EtOAc (750 mL) was added at below 5° C. A solution of 10% NaCl aq. solution (400 mL), water (125 mL) and 1 N HCl solution (100 mL) was slowly added while maintaining the batch temperature at below 5° C. The solution was then adjusted to pH=2 with 1 N HCl (~25 mL). The separated aqueous phase was back-extracted with EtOAc (500 mL). The combined organic phase was washed with 10% NaCl aq. solution (500 mL). After 10% NaCl aq. solution (500 mL) was added to the combined organic phase, the mixed solution was cooled to 0° C. to 5° C. 1 N NaOH aq. solution (~25 mL) was added to adjust the pH=~7. The separated organic phase was filtered through CELITE® (filter aid, Fisher Scientific, Fair Lawn, N.J.) and solvent-switched to IPA at a final volume of 300 mL. AcOH (5.0 mL) was added, and the batch was then heated to reflux for 30 min. The slurry was cooled to 60° C., and water (250 mL) was added dropwise over 1 h. After addition, the batch was aged for additional 30 min before slowly cooling to RT in about 2 h. After aging at least 1 h, the batch was filtered. The wet cake was displacement washed with 50% aq. IPA (100 mL). Suction-drying at RT afforded 56 g of macrocyclic alkyne ester.

$^1$H NMR (400 MHz, CDCl$_3$) δ 7.80 (d, J=9.2 Hz, 1 H), 7.17 (dd, J=9.2, 2.8 Hz, 1 H), 7.04 (d, J=2.8 Hz, 1 H), 5.82 (t, J=4.2 Hz, 1 H), 5.26 (d, J=9.9 Hz, 1 H), 4.62 (dd, J=10.3, 7.3 Hz, 1 H), 4.51 (d, J=11.6 Hz, 1 H), 4.40 (d, J=9.9 Hz, 1 H), 4.03 (dd, J=11.6, 4.4 Hz, 1 H), 3.91 (s, 3 H), 3.87 (m, 1 H), 3.73 (s, 3 H), 2.85 (dt, J=12.1, 4.2 Hz, 1 H), 2.76 (d, J=14.4, 7.3 Hz, 1 H), 2.49 (dt, J=12.2, 5.4 Hz, 1 H), 2.30 (ddd, J=14.6, 10.1, 4.2 Hz, 1 H), 1.99 (m, 1 H), 1.82 (m, 1 H), 1.74 (m, 1 H), 1.08 (s, 9 H), 0.92 (m, 2 H), 0.76 (m, 1 H), 0.47 (m, 1 H).

$^{13}$C NMR (100 MHz, CDCl$_3$) δ 172.3, 171.3, 161.2, 157.4, 156.3, 140.4, 134.3, 130.2, 129.5, 119.5, 105.7, 98.9, 75.5, 75.2, 59.4, 58.1, 55.7, 55.6, 54.1, 52.3, 35.3, 35.0, 29.9, 28.0, 26.3, 18.7, 18.3, 10.3.

IPC HPLC conditions: Ascentis Express C18 column, 100×4.6 mm, 2.7 μm; Column temperature of 40° C.; Flow rate of 1.8 mL/min; and Wavelength of 215 nm.

| Gradiant: | | |
|---|---|---|
| min | CH$_3$CN | 0.1% H$_3$PO$_4$ |
| 0 | 10 | 90 |
| 6 | 95 | 5 |
| 9 | 95 | 5 |
| 9.1 | 10 | 90 |
| Retention times: | | min. |
| De-BOC quinoxaline | | 2.3 |
| Alkyne quinoxaline acid | | 3.3 |
| Alkyne macrocyclic ester | | 5.7 |

Example 14A

Isolation of the Macrocyclic Alkene Ester Anhydrous Form I from Anhydrous Form II and/or Solvate Form

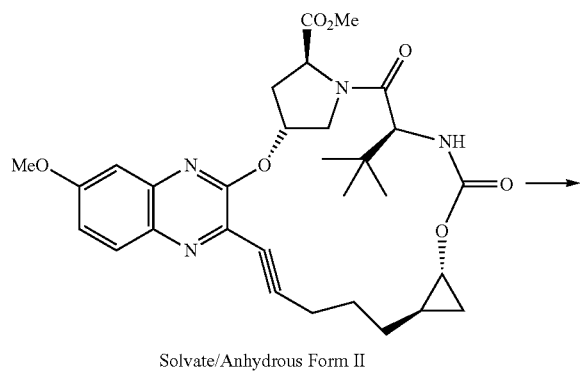

Solvate/Anhydrous Form II

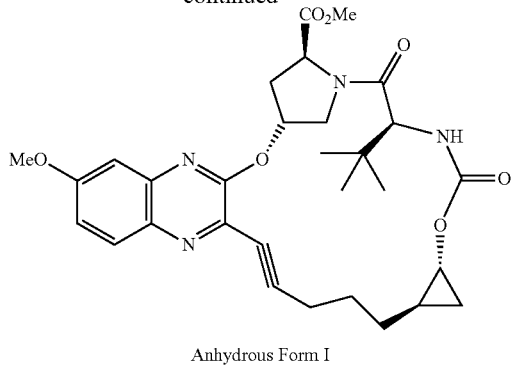

Anhydrous Form I

A slurry of macrocyclic alkyne ester powder (2.9 g) from the prior step in IPA (25 mL) was stirred at 20° C. for 2 h. The batch was filtered and washed with IPA (6 mL). The wet cake was dried at 60° C. under vacuum to give macrocyclic alkyne ester anhydrous Form I, 96% yield.

Figure 3:
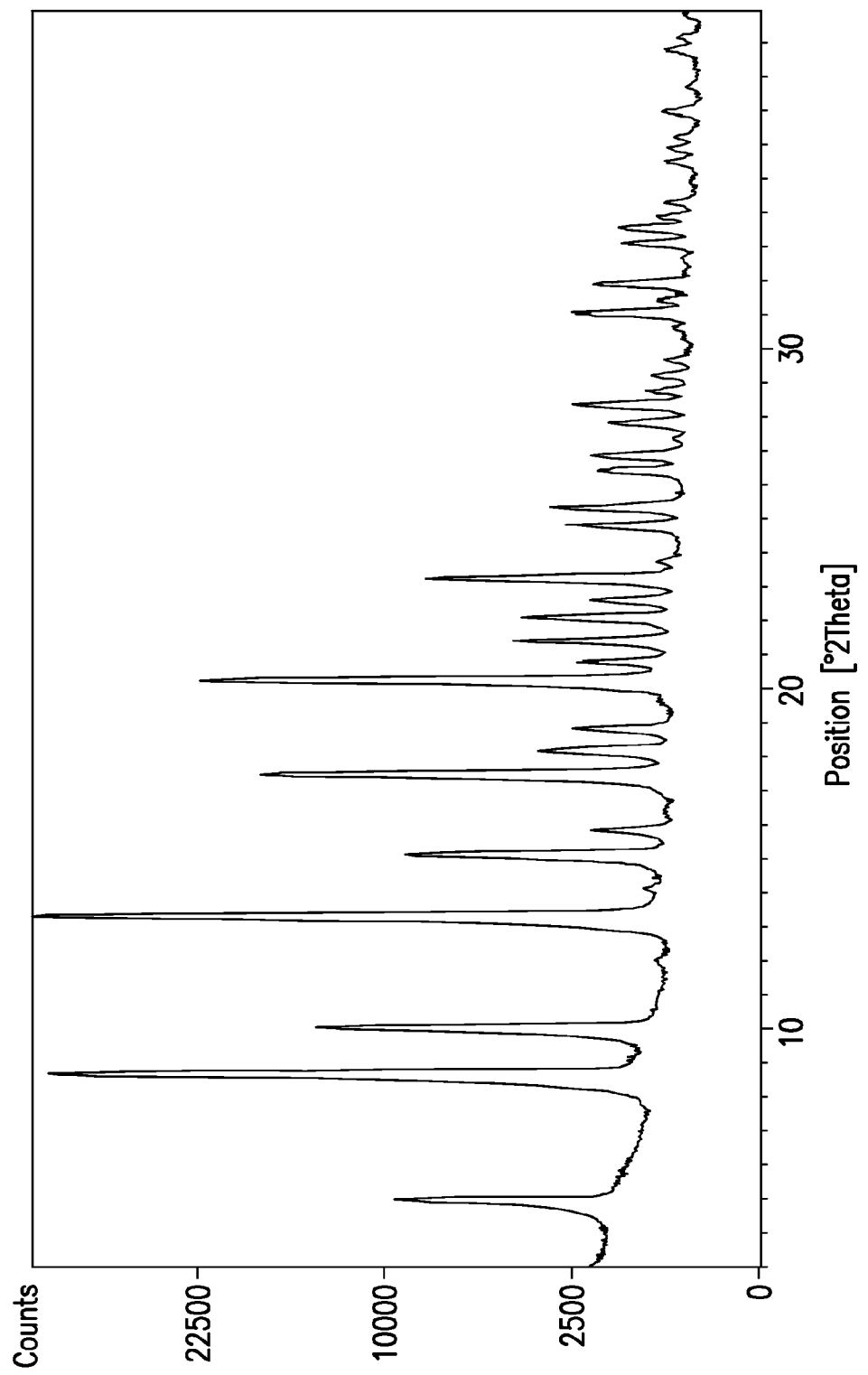
FIG. 3 provides a characteristic X-ray diffraction pattern for the crystalline macrocyclic alkyne ester anhydrous form I of Example 14A.

An X-ray powder diffraction pattern was generated to characterize the molecular structure of the macrocyclic alkyne ester anhydrous Form I. The pattern was generated as described above in Example 10. The pattern, shown in FIG. 3, exhibited characteristic reflections corresponding to d-spacings as follows.

| Position [° 2θ] | d-spacing [Å (Å = 0.1 nm)] | Relative Intensity [%] |
|---|---|---|
| 5.0 | 17.5 | 19.9 |
| 8.7 | 10.1 | 76.1 |
| 10.1 | 8.8 | 29.2 |
| 13.4 | 6.6 | 100.0 |
| 15.1 | 5.9 | 23.7 |
| 17.6 | 5.1 | 44.0 |
| 20.3 | 4.4 | 64.2 |
| 21.4 | 4.1 | 11.6 |
| 22.2 | 4.0 | 8.8 |
| 23.3 | 3.8 | 22.3 |

In addition to the X-ray powder diffraction patterns described above, Anhydrous Form I was further characterized by solid-state carbon-13 nuclear magnetic resonance ($^{13}$C NMR) spectra. The $^{13}$C NMR spectra were recorded using a Bruker 4 mm HXY triple resonance CPMAS, and a Bruker 4 mm H/FX double resonance CPMAS probe, respectively. The $^{13}$C NMR spectra were collected utilizing proton/$^{13}$C variable-amplitude cross-polarization (VACP) with a contact time of 3 ms, and a pulse delay of 4 s, while magic-angle spinning (MAS) the samples at 13 kHz. A line broadening of 30 Hz was applied to the $^{13}$C NMR spectra before Fourier Transformation. Chemical shifts are reported on the TMS scale using the carbonyl carbon of glycine (176.7 ppm.) as a secondary reference. FIG. 4 shows the solid state $^{13}$C CPMAS NMR spectrum for the crystalline Anhydrous Form I. Characteristic peaks for Anhydrate I are observed at 172.4, 171.7, 161.5, 157.7, 142.0, 135.3, 130.2, 112.7, 112.1, 97.3, 77.2, 75.0, 60.3, 59.3, 57.0, 55.3, 54.4, 37.2, 34.9, 30.5, 27.9, 20.9, 19.4, and 10.5 ppm.

Figure 5:
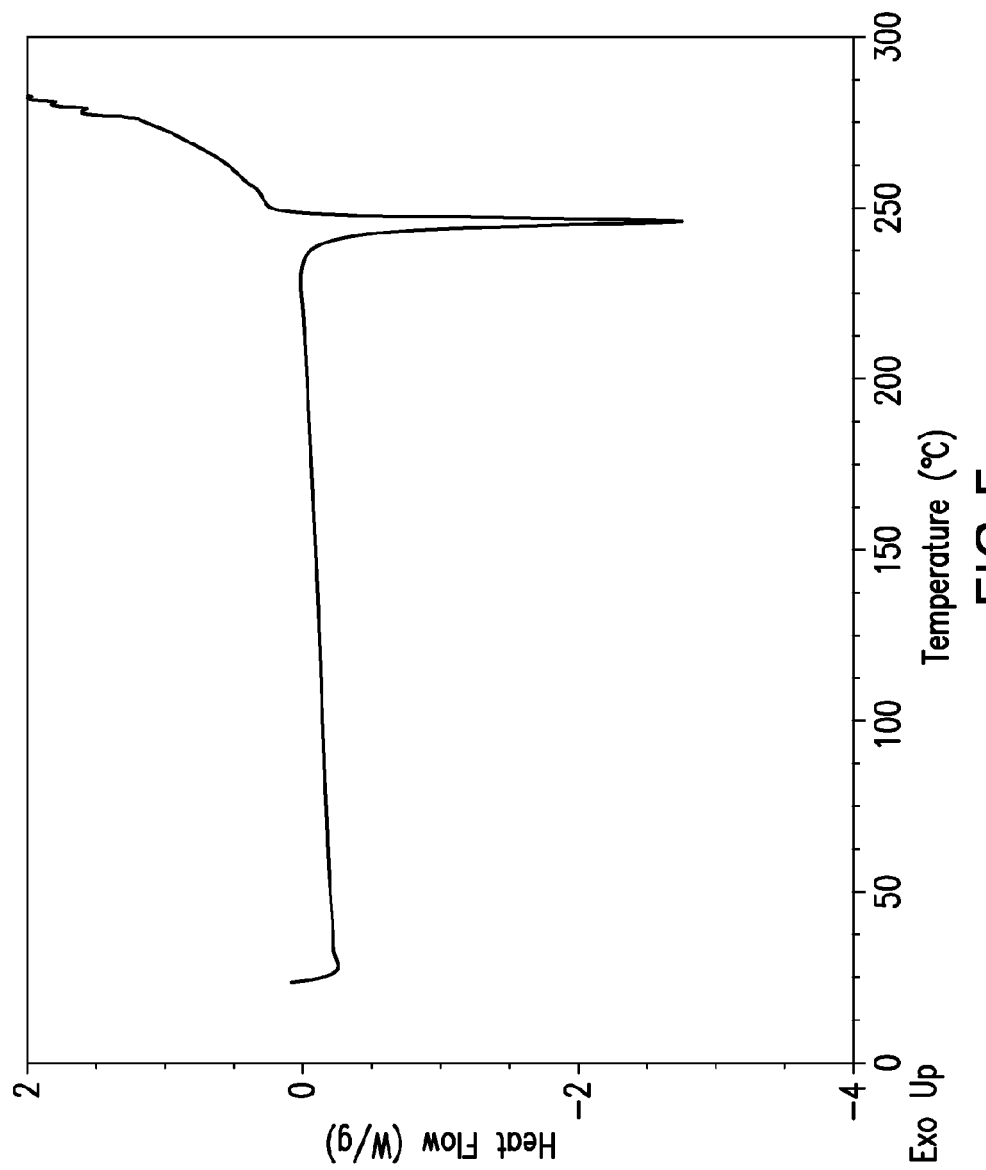
FIG. 5 provides a typical differential scanning calorimetry (DSC) curve of the crystalline macrocyclic alkyne ester anhydrous form I of Example 14A.

Further, a differential scanning calorimetry (DSC) curve was prepared. DSC data are acquired using TA Instruments DSC 2910 or equivalent. Between 2 mg and 6 mg sample is weighed into a pan and covered. This pan is then covered and placed at the sample position in the calorimeter cell. An empty pan is placed at the reference position. The calorimeter cell is closed and a flow of nitrogen is passed through the cell. The heating program is set to heat the sample at a heating rate of 10° C./min to a temperature of approximately 300° C. The heating program is started. When the run is completed, the data are analyzed using the DSC analysis program contained in the system software. The thermal events are integrated between baseline temperature points that are above and below the temperature range over which the thermal event is observed. The data reported are the onset temperature, peak temperature and enthalpy. FIG. 5 shows a typical DSC curve for the crystalline Anhydrous Form I.

Example 14B

Preparation of Macrocyclic Alkyne Ester Isopropyl Alcohol/Water Solvate and Anhydrous Form II from Anhydrous Form I

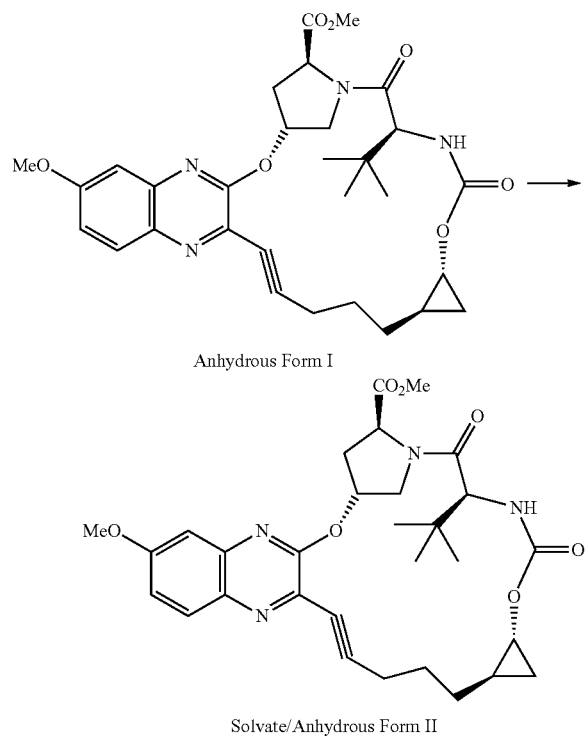

Anhydrous Form I

Solvate/Anhydrous Form II

To a solution of IPA (62.1 mL), EtOAc (16.2 mL), and water (45 mL) was charged macrocyclic alkyne ester anhydrous Form I powder (10 g). The resulting slurry was stirred at 20° C. Then, macrocyclic alkyne ester solvate seeds (0.156 g) were added. The batch was aged at 50° C. to 65° C. for 30 min, and cooled to 10° C. over 2 h. After aging at 10° C. for 1.5 h, the batch was heated to 50° C. to 65° C. and aged at 50° C. to 65° C. for 3 h before cooling to 10° C. The heating-cooling cycle was repeated several times until the anhydrous Form I was converted to the IPA/water solvate. The solvate was filtered and washed with 40 mL of 50% aqueous IPA. The wet cake was dried at 60° C. under vacuum to give the anhydrous Form II. 95% yield. Anhydrous Form II can also be prepared by heating the corresponding IPA solvate/hydrate to >150° C.

An X-ray powder diffraction pattern was generated to characterize the molecular structure of the crystalline macrocyclic alkyne ester anhydrous Form II. The pattern was generated as described above and in Example 10. The pattern, shown in FIG. 6, exhibited characteristic reflections corresponding to d-spacings as follows.

| Position [° 2 θ] | d-spacing [Å (Å = 0.1 nm)] | Relative Intensity [%] |
|---|---|---|
| 7.2 | 12.3 | 58.6 |
| 9.3 | 9.5 | 54.5 |
| 10.9 | 8.1 | 20.8 |
| 11.3 | 7.8 | 39.1 |
| 14.7 | 6.0 | 88.1 |
| 18.9 | 4.7 | 71.8 |
| 22.8 | 3.9 | 100.0 |
| 23.8 | 3.7 | 35.6 |
| 25.1 | 3.6 | 21.0 |

Figure 7:
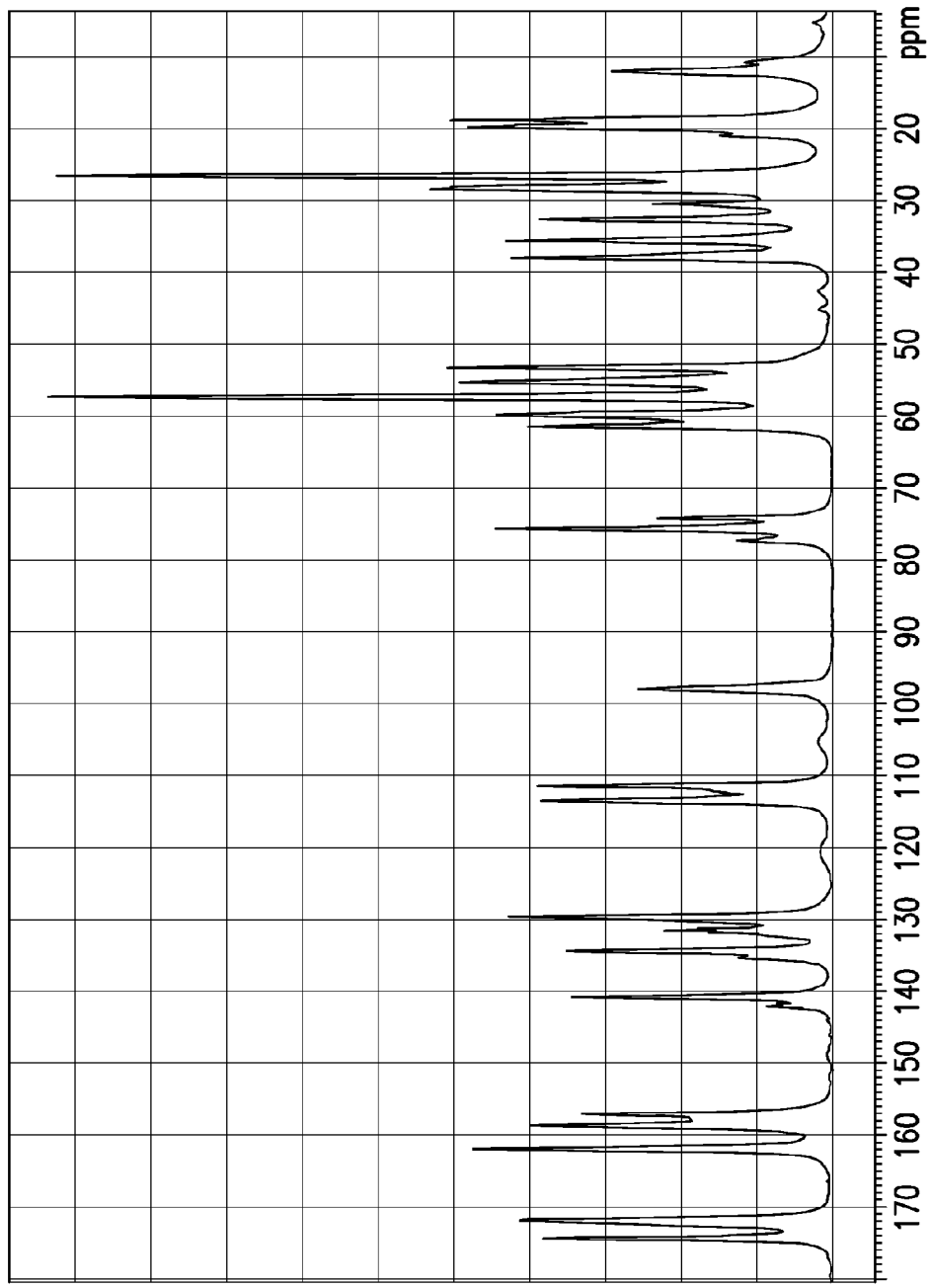
FIG. 7 provides a characteristic $^{13}C$ NMR spectrum for the crystalline macrocyclic alkyne ester anhydrous form II of Example 14B.

In addition to the X-ray powder diffraction patterns described above, the crystalline macrocyclic alkyne ester anhydrous Form II were further characterized by solid-state carbon-13 nuclear magnetic resonance ($^{13}$C NMR) spectra. The $^{13}$C NMR spectra were recorded as described above. FIG. 7 shows the solid state $^{13}$C CPMAS NMR spectrum for the crystalline macrocyclic alkyne ester anhydrous Form II. Characteristic peaks are observed at 174.2, 171.7, 161.9, 158.6, 157.0, 140.7, 134.4, 131.4, 129.6, 113.4, 111.3, 97.9, 75.6, 74.1, 61.3, 59.7, 57.2, 55.2, 53.2, 37.8, 35.5, 32.6, 30.5, 28.3, 26.5, 19.7, 18.7 and 12.0 ppm.

Figure 8:
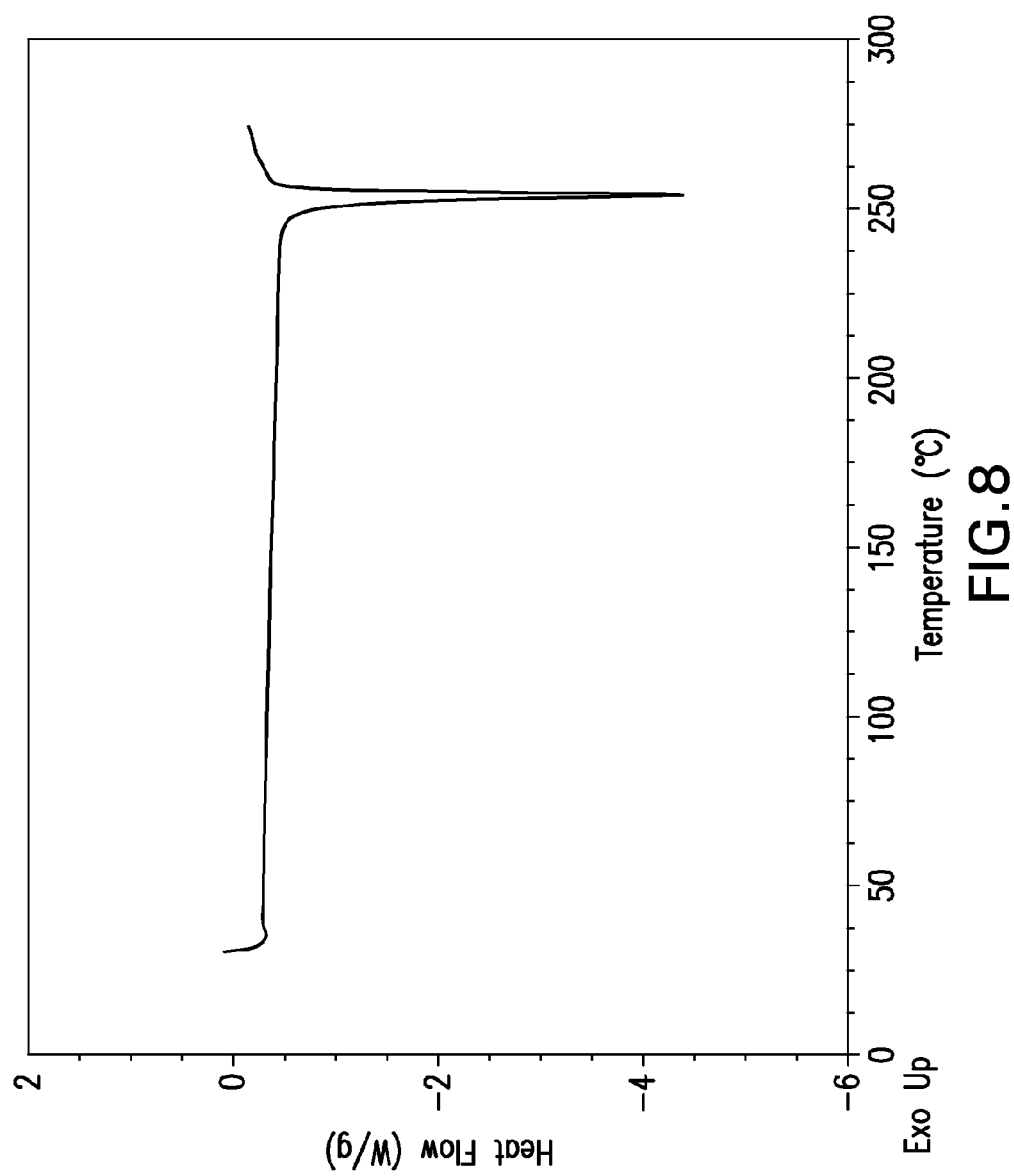
FIG. 8 provides a typical differential scanning calorimetry (DSC) curve of the crystalline macrocyclic alkyne ester anhydrous form II of Example 14B.

Further, a differential scanning calorimetry (DSC) curve was prepared as described above. FIG. 8 shows a typical DSC curve for the crystalline macrocyclic alkyne ester anhydrous Form II.

Example 14C

Preparation of Macrocyclic Alkyne Ester Isopropyl Alcohol/Water Solvate

The IPA/water co-solvate/hydrate of macrocyclic alkyne ester is prepared in mixtures of IPA/water ranging from 4 wt % water in IPA at 15° C. to above 12 wt % water in IPA at 60° C.

An X-ray powder diffraction pattern was generated to characterize the molecular structure of the crystalline IPA solvate/hydrate. The pattern was generated as described above and in Example 10. The pattern, shown in FIG. 9, exhibited characteristic reflections corresponding to d-spacings as follows.

| Position [° 2 θ] | d-spacing [Å (Å = 0.1 nm)] | Relative Intensity [%] |
|---|---|---|
| 6.7 | 13.3 | 4.9 |
| 8.4 | 10.6 | 100.0 |
| 13.4 | 6.6 | 17.9 |
| 14.9 | 6.0 | 17.0 |
| 15.6 | 5.7 | 11.4 |
| 16.0 | 5.5 | 29.4 |
| 17.7 | 5.0 | 26.7 |
| 19.1 | 4.7 | 28.8 |
| 19.8 | 4.5 | 16.1 |
| 23.7 | 3.8 | 45.4 |
| 25.5 | 3.5 | 25.3 |

Figure 10:
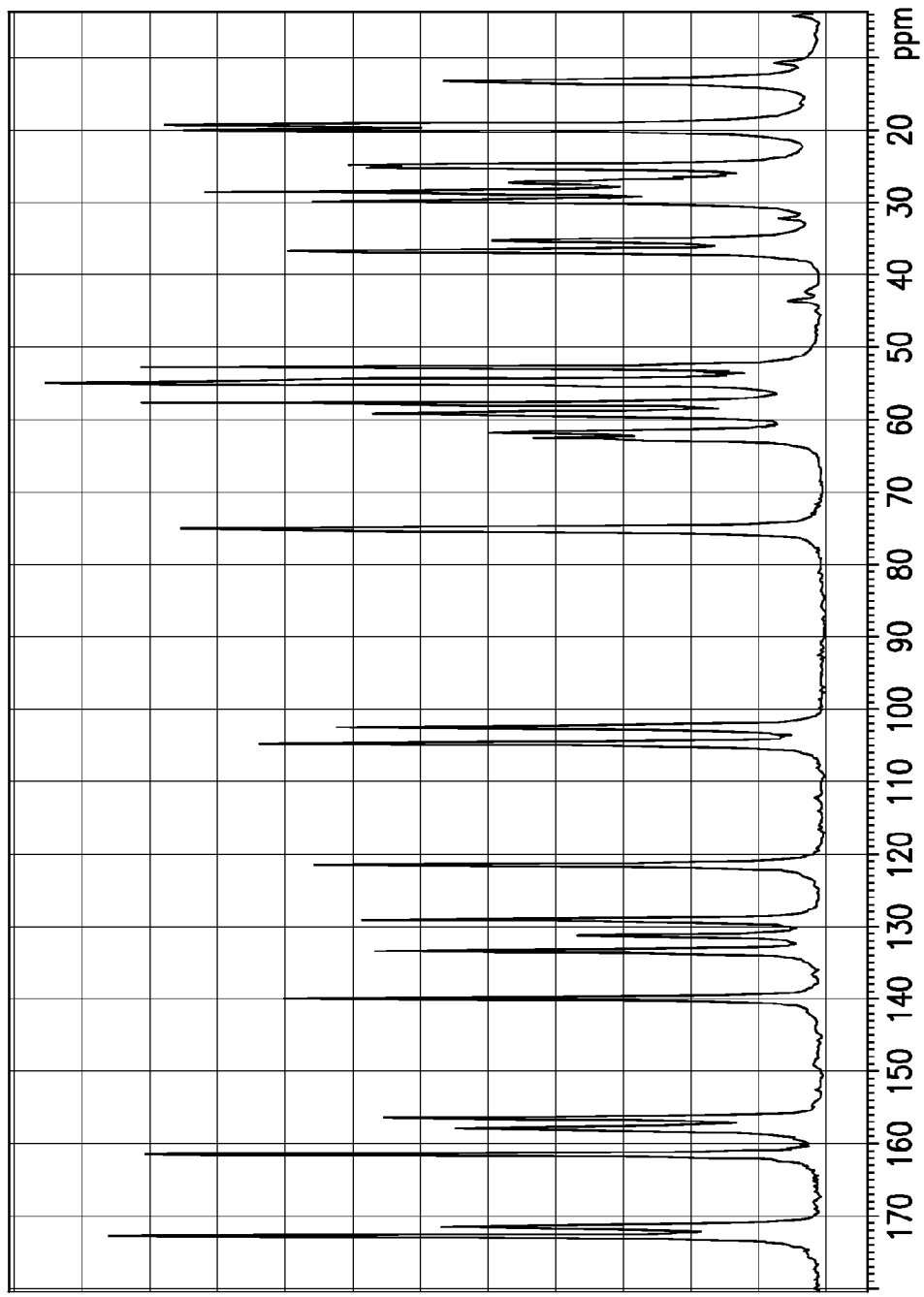
FIG. 10 provides a characteristic $^{13}C$ NMR spectrum for the crystalline macrocyclic alkyne ester anhydrous form II of Example 14C.

In addition to the X-ray powder diffraction patterns described above, the crystalline IPA solvate/hydrate was further characterized by solid-state carbon-13 nuclear magnetic resonance ($^{13}$C NMR) spectra. The $^{13}$C NMR spectra were recorded as described above. FIG. 10 shows the solid state $^{13}$C CPMAS NMR spectrum for the crystalline IPA solvate/hydrate. Characteristic peaks are observed at 172.7, 171.4, 161.4, 157.7, 156.3, 139.8, 133.3, 131.2, 129.0, 121.4, 104.6, 102.4, 74.9, 62.5, 61.7, 59.1, 57.6, 54.8, 52.7, 36.6, 35.2, 29.8, 28.4, 27.2, 25.1, 24.8, 19.9, 19.2 and 13.2 ppm.

Figure 11:
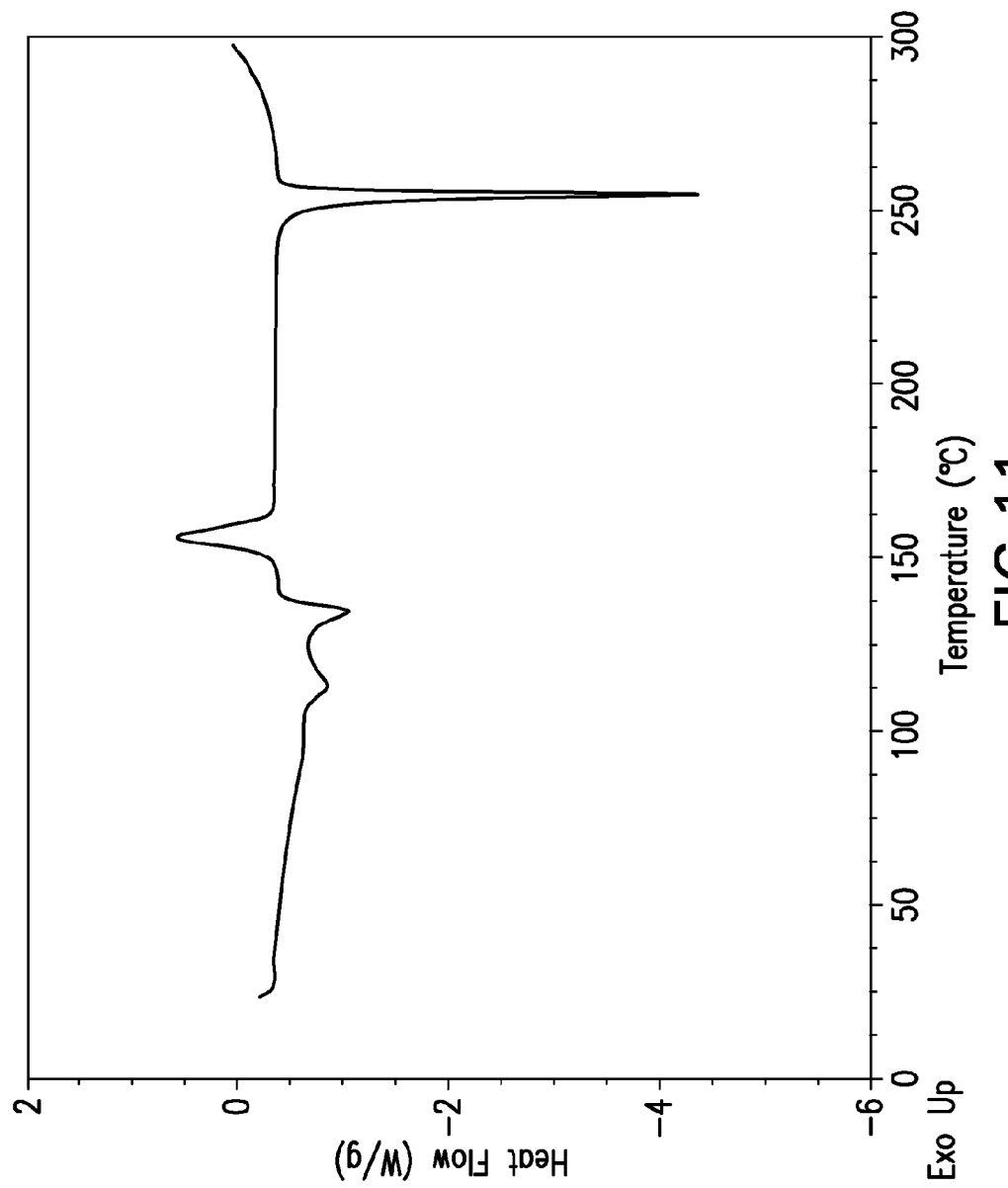
FIG. 11 provides a typical differential scanning calorimetry (DSC) curve of the crystalline IPA/water mixed solvate/hydrate of Example 14C.

Further, a differential scanning calorimetry (DSC) curve was prepared as described above. FIG. 11 shows a typical DSC curve for the crystalline IPA solvate/hydrate.

Example 15

Preparation of Macrocyclic Ester

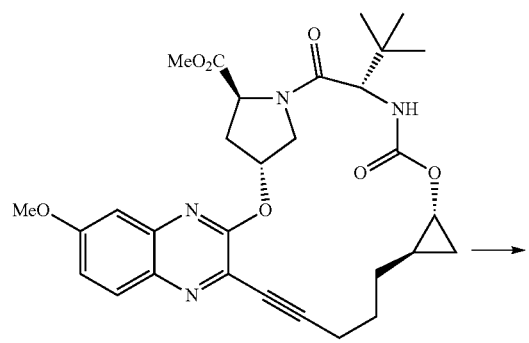

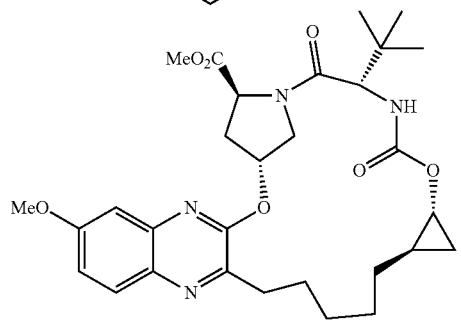

A mixture of the alkyne macrocyclic ester from Example 13 (10.0 g, 17.71 mmol) and 5% Pd/C 50% wet (3.5 g, 0.822 mmol) in THF (100 mL) was hydrogenated at RT under 40 psig of H$_2$ for at least 10 h. Upon reaction completion, the batch was filtered through CELITE® (filter aid, Fisher Scientific, Fair Lawn, N.J.), and the filtered catalyst was washed with THF (100 mL). The combined filtrate was solvent-switched to IPA in vacuum at a final volume of ~50 mL. The slurry was heated up to reflux for about 1 h. The batch was then cooled to 50° C. and water (30 mL) was added dropwise over 1 h. The batch was slowly cooled to below 0° C. over 2 h and stirred at 0° C. for additional 1 h before filtration. The wet cake was washed with a cold solution (0° C. to 5° C.) of 57% IPA in water (17.5 mL). Suction drying at RT gave 8.5 g of the desired macrocyclic ester.

$^1$H NMR (400 MHz, CDCl$_3$) δ 7.83 (d, J=9.2 Hz, 1 H), 7.18 (dd, J=9.2, 2.8 Hz, 1 H), 7.1 (d, J=2.8 Hz, 1 H), 5.98 (t, J=4.0 Hz, 1 H), 5.24 (d, J=9.9 Hz, 1 H), 4.60 (dd, J=10.7, 7.3 Hz, 1 H), 4.46 (d, J=11.9 Hz, 1 H), 4.40 (d, J=10.0 Hz, 1 H), 4.01 (dd, J=11.6, 4.0 Hz, 1 H), 3.93 (s, 3 H), 3.80 (m, 1 H), 3.75 (s, 3 H), 2.90 (ddd, J=13.7, 11.5, 4.8 Hz, 1 H), 2.79 (ddd, J=13.7, 12.1, 4.8 Hz, 1 H), 2.69 (dd, J=14.2, 6.5 Hz, 1 H), 2.28 (ddd, J=14.5, 10.7, 4.3 Hz, 1 H), 1.76 (m, 2 H), 1.66 (m, 2 H), 1.52 (m, 3 H), 1.09 (s, 9 H), 0.99 (m, 1 H), 0.92 (m, 1 H), 0.67 (m, 1 H), 0.46 (m, 1 H).

$^{13}$C NMR (100 MHz, CDCl$_3$) δ 172.4, 171.5, 160.4, 157.5, 155.1, 148.7, 140.1, 134.6, 129.4, 118.7, 106.1, 74.4, 59.4, 58.2, 55.8, 55.5, 54.4, 52.5, 35.7, 35.2, 34.0, 30.9, 29.5, 28.6, 28.3, 26.5, 18.9, 11.2.

IPC HPLC conditions: Ascentis Express C18 Column, 100×4.6 mm, 2.7 μm; Column temperature or 40° C.; Flow rate or 1.8 mL/min; and Wavelength of 215 nm.

| Gradiant: | | |
|---|---|---|
| min | CH$_3$CN | 0.1% H$_3$PO$_4$ |
| 0 | 10 | 90 |
| 6 | 95 | 5 |
| 9 | 95 | 5 |
| 9.1 | 10 | 90 |

| Retention times: | min. |
|---|---|
| Alkyne macrocyclic ester | 5.7 |
| cis-Alkene macrocclic ester (reaction intermediate) | 6.0 |
| trans-Alkene macrocclic ester (reaction intermediate) | 6.0 |
| Product of Example 15 | 6.2 |

Example 16

Preparation of Macrocyclic Acid

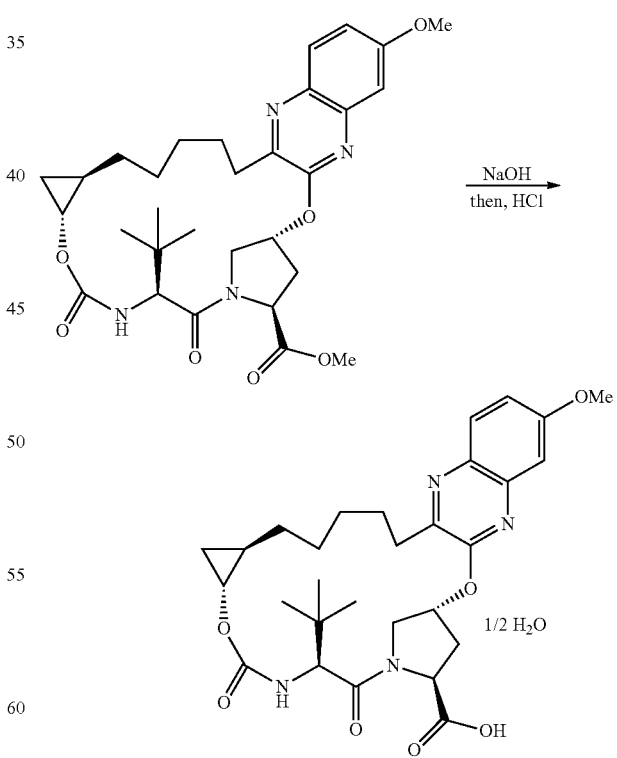

To a slurry of macrocyclic ester from Example 14 (90 g, 158.3 mmol) in MeOH (720 mL) at RT was added 2 M NaOH (237.4 mL, 475 mmol) dropwise. The reaction mixture was aged at 50° C. for 2 h to 3 h. The reaction solution was cooled to 35° C. to 40° C., and 5 N HCl in 50% aq MeOH (70 mL) was added dropwise. The batch was seeded with free acid hemihydrate (~100 mg) and aged for 30 min to 1 h at 40° C. Additional 5 N HCl in 50% aq MeOH (30 mL) was added dropwise over 2 h to 4 h at 40° C. The slurry was aged additional 1 h before cooling to RT. The slurry was aged for additional 1 h before filtration. The wet cake was washed with 65% MeOH in water (3×270 mL, displacement wash, slurry wash and displacement wash). Suction drying at RT or vacuum-oven drying with dry $N_2$ sweep at 60° C. to 80° C. gave 85.6 g of macrocyclic acid hemihydrate as an off-white solid.

$^1$H NMR (400 MHz, CDCl$_3$) δ 7.85 (d, J=9.0 Hz, 1 H), 7.19 (dd, J=9.0, 2.8 Hz, 1 H), 7.13 (d, J=2.8 Hz, 1 H), 5.99 (t, J=3.9 Hz, 1 H), 5.45 (d, J=9.9 Hz, 1 H), 4.80 (s, br, 2 H, COOH, hemihydrate H$_2$O), 4.64 (dd, J=10.4, 7.4 Hz, 1 H), 4.49 (d, J=11.6 Hz, 1 H), 4.44 (d, J=10.0 Hz, 1 H), 3.99 (dd, J=11.7, 4.0 Hz, 1 H), 3.94 (s, 3 H), 3.81 (m, 1 H), 2.90 (ddd, J=13.8, 11.8, 4.8, 1 H), 2.80 (ddd, J=13.8, 11.8, 4.8 Hz, 1 H), 2.71 (dd, J=14.3, 7.3, 1 H), 2.42 (ddd, J=14.4, 10.6, 4.2 Hz, 1 H), 1.76 (m, 2 H), 1.66 (m, 2 H), 1.52 (m, 3 H), 1.07 (s, 9 H), 0.96 (m, 2 H), 0.67 (m, 1 H), 0.47 (m, 1 H).

$^{13}$C NMR (100 MHz, CDCl$_3$) δ 174.5, 172.1, 160.5, 157.6, 155.1, 148.6, 141.0, 134.3, 129.1, 118.9, 106.1, 74.3, 59.6, 58.3, 55.6, 54.6, 35.6, 35.3, 33.7, 30.8, 29.4, 28.6, 28.3, 26.5, 18.9, 11.2.

IPC HPLC conditions: Hypersil Gold PFP Column, 150× 4.6 mm, 3.0 µm, Column temperature of 40° C.; Flow rate of 1.8 mL/min; and Wavelength of 215 nm.

| Gradiant: | | |
|---|---|---|
| min | CH$_3$CN | 0.1% H$_3$PO$_4$ |
| 0 | 25 | 75 |
| 12 | 80 | 20 |
| 12.1 | 25 | 75 |
| 14 | 25 | 75 |
| Retention times: | min. | |
| Product of Example 15 | 6.78 | |
| Product of Example 16 | 5.41 | |

Example 17

Preparation of Compound A, Method A

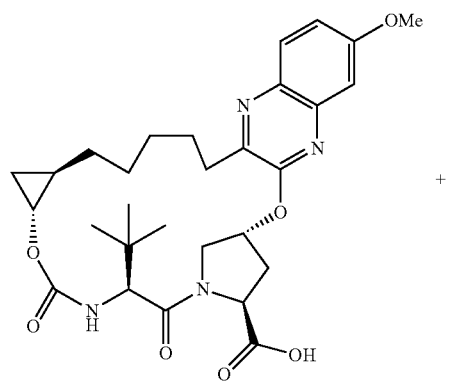

+

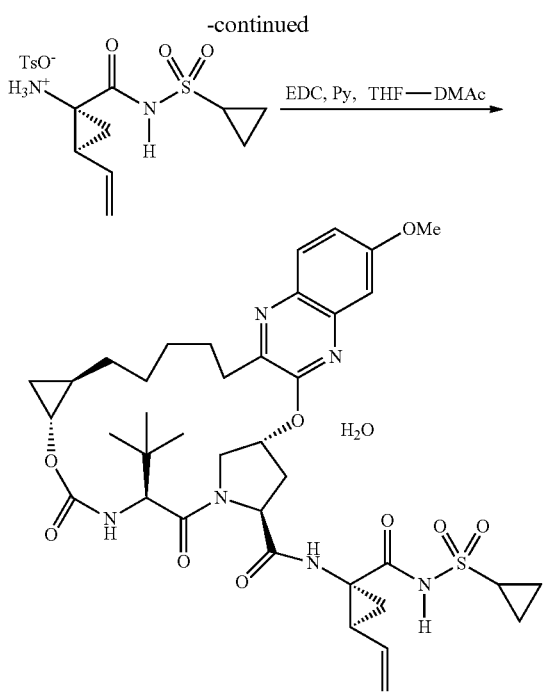

Macrocyclic acid hemihydrate, the product of Example 15 (10.16 g, 18.03 mmol) was dissolved in THF (50 mL to 90 mL). The solution was azetropically dried at a final volume of 100 mL. Sulfonamide pTSA salt (7.98 g, 1.983 mmol) followed by DMAc (15 mL) was added at RT. The batch was cooled to 0° C. to 10° C., and pyridine (10 mL) was added dropwise. Then, EDC HCl (4.49 g, 23.44 mmol) was added in portions or one portion at 0° C. to 10° C. The reaction mixture was aged at 0° C. to 10° C. for 1 h, and then warmed to 15° C. to 20° C. for 2 h to 4 h. MeOAc (100 mL) followed by 15 wt % citric acid in 5% NaCl in water (50 mL) was added, while the internal temperature was maintained to <25° C. with external cooling. The separated organic phase was washed with 15 wt % citric acid in 5% NaCl in water (50 mL) followed by 5% NaCl (50 mL). The organic phase was solvent-switched to acetone at a final volume of =80 mL. Water (10 mL) was added dropwise at 35° C. to 40° C. The batch was seeded with Compound A monohydrate form III (=10 mg) and aged for 0.5 h to 1 h at 35° C. to 40° C. Additional water (22 mL) was added dropwise over 2 h to 4 h at 35° C. to 40° C. The slurry was aged at 20° C. for 2 h to 4 h before filtration. The wet cake was displacement washed with 60% acetone in water (2×40 mL). Suction drying at RT gave Compound A monohydrate form III as a white solid.

$^1$H NMR (400 MHz, CDCl$_3$) δ 9.95 (s, br, 1 H), 7.81 (d, J=9.1 Hz, 1 H), 7.18 (dd, J=9.1, 2.7 Hz, 1 H), 7.16 (s, br, 1 H), 7.13 (d, J=2.7 Hz, 1 H), 5.96 (t, J=3.8 Hz, 1 H), 5.72 (m, 1 H), 5.68 (d, J=10.1 Hz, 1 H), 5.19 (d, J=17.1 Hz, 1 H), 5.07 (d, J=10.1 Hz, 1 H), 4.52 (d, J=11.4 Hz, 1 H), 4.45 (d, J=9.8 Hz, 1 H), 4.36 (d, J=10.5, 6.9 Hz, 1 H), 4.05 (dd, J=11.5, 3.9 Hz, 1 H), 3.93 (s, 3 H), 3.78 (m, 1 H), 2.90 (m, 1 H), 2.82 (tt, J=8.0, 4.8 Hz, 1 H), 2.74 (dt, J=13.2, 4.8 Hz, 1 H), 2.59 (dd, J=14.0, 6.7 Hz, 1 H), 2.40 (ddd, J=14.0, 10.6, 4.0 Hz, 1 H), 2.10 (dd, J=17.7, 8.7 Hz, 1 H), 1.98 (2 H, mono hydrate H$_2$O), 1.88 (dd, J 8.2, 5.9 Hz, 1 H0, 1.74 (m, 3 H), 1.61 (m, 1 H), 1.50 (m, 3 H), 1.42 (dd, J=9.6, 5.8 Hz, 1 H), 1.22 (m, 2 H), 1.07 (s, 9 H), 0.95 (m, 4 H), 0.69 (m, 1 H), 0.47 (m, 1 H).

¹³C NMR (100 MHz, CDCl₃) δ 173.5, 172.1, 169.1, 160.4, 157.7, 154.9, 148.4, 141.0, 134.3, 132.7, 129.1, 118.8, 118.7, 106.5, 74.4, 59.6, 59.4, 55.8, 55.5, 54.9, 41.8, 35.4, 35.3, 35.2, 34.3, 31.2, 30.7, 29.5, 28.6, 28.2, 26.6, 22.6, 18.7, 11.2, 6.31, 6.17.
HPLC conditions: Ascentis Express Column, 10 cm×4.6 mm, 2.7 μm; Column temperature of 40° C.; Flow rate of 1.8 mL/min; and Wavelength of 215 nm.
| Gradiant: | | |
|---|---|---|
| min | CH₃CN | 0.1% H₃PO₄ |
| 0 | 20 | 80 |
| 5 | 55 | 45 |
| 15 | 55 | 45 |
| Gradiant: | | |
|---|---|---|
| 25 | 95 | 5 |
| 27 | 95 | 5 |
| 27.1 | 20 | 80 |
| 32 | 20 | 80 |
| Retention time: | | min. |
| Compound A | | 14.50 |
Example 18
Preparation of Compound A, Method B
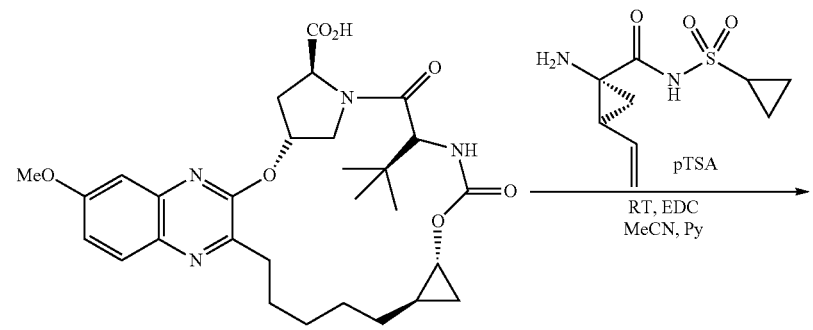
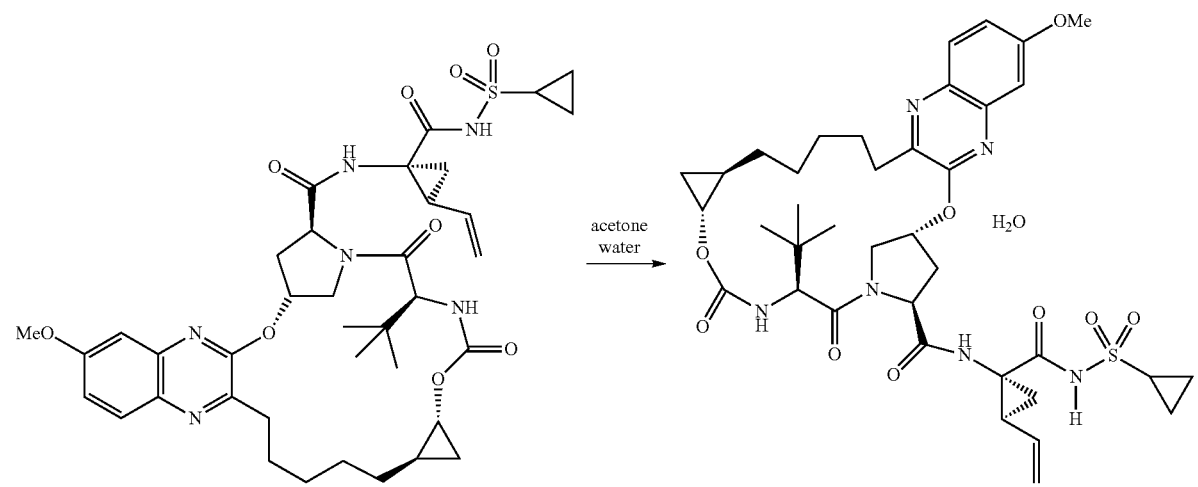

To a 50-L flask equipped with overhead stirring was added macrocyclic acid (1.06 kg crude, 1.00 eq), amine-pTSA (862 g crude, 1.12 eq) and MeCN (7.42 L) at 19° C. The slurry was cooled in a water bath, pyridine (2.12 L, 13.8 eq) was added, aged 15 min, and then added EDC (586 g, 1.60 eq) in one portion, aged 1.5 h, while it turned into a clear homogeneous solution.

The solution cooled in a water bath, then quenched with 2 N HCl (1.7 L), and seeded (9.2 g), aged 15 min, and the rest of the aqueous HCl was added over 2.5 h. A yellow slurry was formed. The slurry was aged overnight at RT, filtered, washed with MeCN/water (1:1 v/v, 8 L), to obtain Compound A (Hydrate II).

Compound A was dissolved in acetone (4 L) at RT, filtered and transferred to a 12-L round-bottom flask with overhead stirring, rinsed with extra acetone (1 L), heated to 50° C., water (0.9 L) was added, seeded with Compound A monohydrate form III (~10 mg), and aged 15 min, and then added water (0.8 L) over 2.5 h, extra water 3.3 v over 2.5 h was added, stopped heating, cooled to RT, aged at RT overnight, filtered, washed with water/acetone (1:1 v/v, 4 L), and dried in air under vacuum. Compound A Hydrate III, 670 g, was obtained as an off-white solid.

Example 19

Preparation of Compound A, Method C

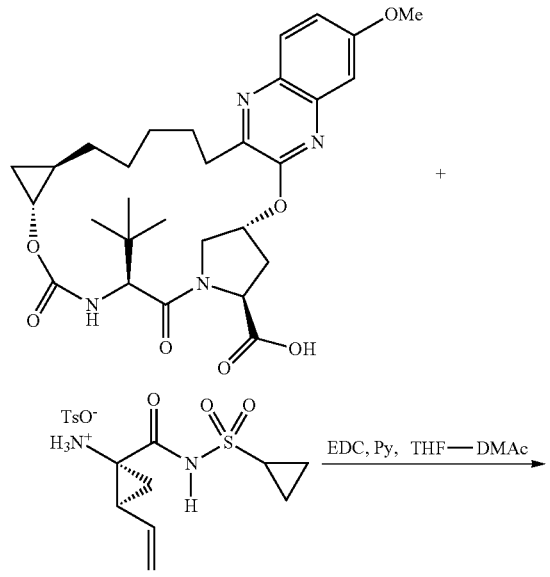

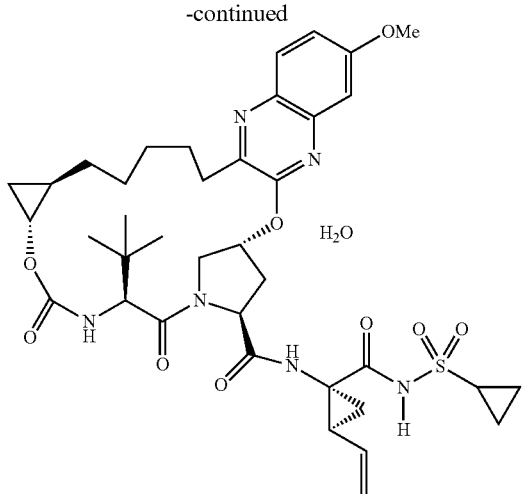

Macrocyclic acid hemihydrate from Example 15 (10.16 g, 18.03 mmol) was dissolved in THF (50 ml to 90 mL). The solution was azetropically dried at a final volume of 100 mL. Sulfonamide pTSA salt (7.98 g, 19.83 mmol) was added, followed by DMAc (15 mL), at RT. The batch was cooled to 0° to 10° C., and pyridine (10 mL) was added dropwise. Then, EDC HCl (4.49 g, 23.44 mmol) was added (in portions or one portion) at 0° C. to 10° C. The reaction mixture was aged at 0° C. to 10° C. for 1 h, and then warmed to 15° C. to 20° C. for 2 h to 4 h. THF (50 mL) was added, followed by 15 wt % citric acid in 15 wt % aq. NaCl (50 mL), while the internal temperature was maintained at <25° C. with external cooling. The separated organic phase was washed with 15 wt % citric acid in 15% aq. NaCl (40 mL), followed by 15% NaCl (40 mL). The organic phase was solvent-switched to acetone at a final volume of =75 mL. Water (11 mL to 12 mL) was added dropwise at 35° C. to 40° C. The batch was seeded with Compound A monohydrate form III (~20 mg) and aged for 0.5 h to 1 h at 35° C. to 40° C. Additional water (22 mL) was added dropwise over 2 h to 4 h at 35° C. to 40° C. The slurry was aged at 20° C. for 2 h to 4 h before filtration. The wet cake was displacement washed with 60% acetone in water (40 mL×2). Suction drying at RT or vacuum-oven drying at 45° C. gave Compound A monohydrate form III as a white solid.

Example 20

Preparation of Compound A, Method D

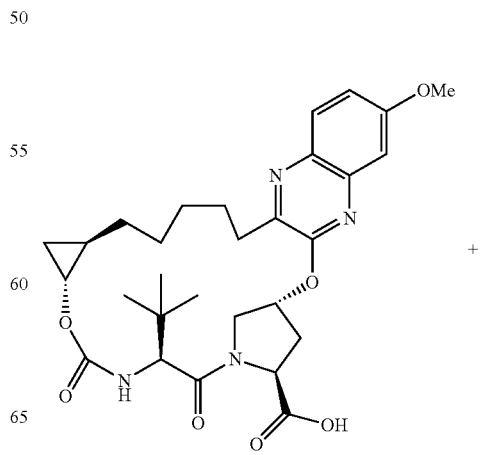

-continued

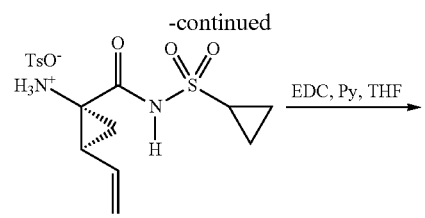

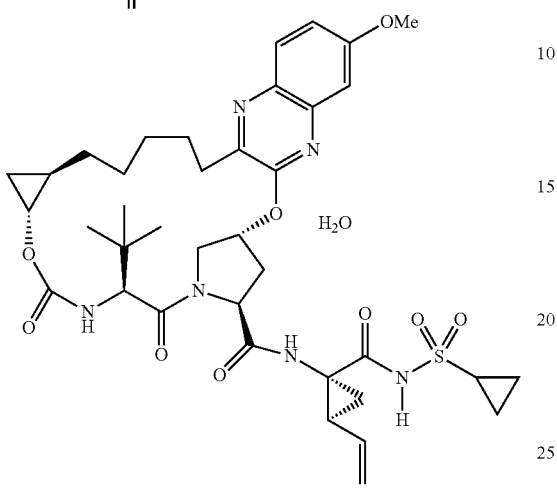

Macrocyclic acid hemihydrate from Example 12 (10 g, 98.4 wt %, 17.74 mmol) was dissolved in THF (70 mL). The solution was azetropically dried at a final volume of ~60 mL. Sulfonamide pTSA salt (7.53 g, 18.7 mmol) was added at RT. The batch was cooled to 0° C. to 5° C., and pyridine (11.4 mL) was added dropwise. Then, EDC HCl (4.26 g, 22.2 mmol) was added in portions at 0° C. to 15° C. The reaction mixture was aged at 10° C. to 15° C. for 2 h to 4 h. 35 wt % Citric acid in 10 wt % aq. NaCl (80 mL) was added, while the internal temperature was maintained at <25° C. with external cooling. The separated organic phase was solvent-switched to acetone at a final volume of ~75 mL. Water (12 mL) was added dropwise at 50° C. The batch was seeded with Compound A monohydrate form III (~300 mg) and aged for 0.5 h to 1 h at 50° C. Additional water (25 mL) was added dropwise over 6 h at 35° C. to 40° C. The slurry was aged at 20° C. for 2 h to 4 h before filtration. The wet cake was displacement washed with 65% acetone in water (40 mL). Suction drying at RT or vacuum-oven drying at 45° C. gave Compound A monohydrate form III as a white solid.

It will be appreciated that various of the above-discussed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

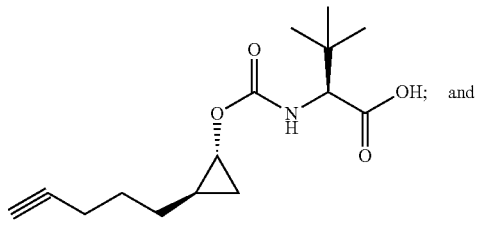

and (6) optionally converting
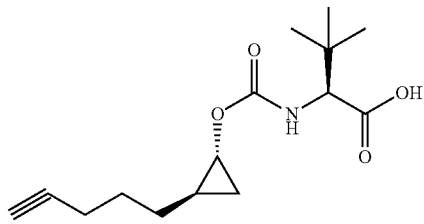
to a salt thereof.
13. A method of preparing Compound A:
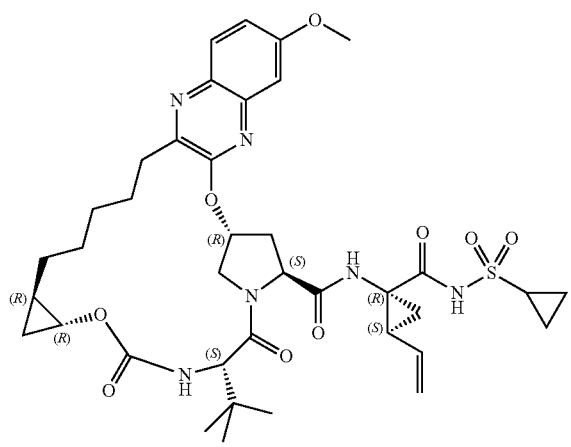
or a pharmaceutically acceptable salt thereof, said method comprising:
(a) producing a compound of Formula B according to claim 12,
(b) reacting
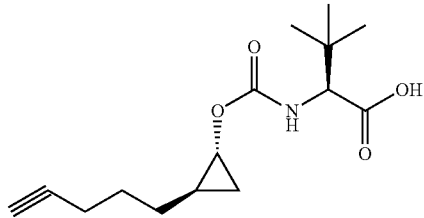
with
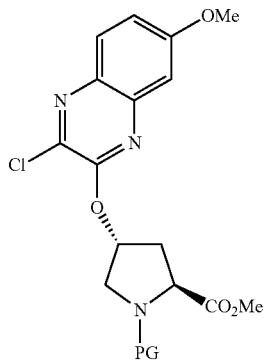
to produce
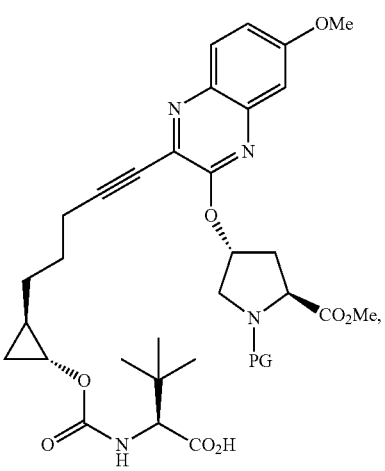
where PG is H or a protecting group selected from —OSiR$^8$ and —OR$^8$;
(c) and further comprising the steps of:
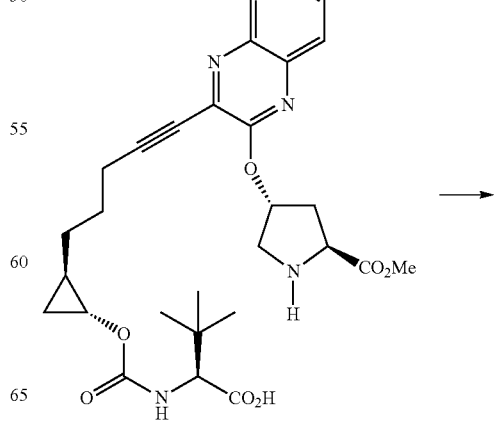

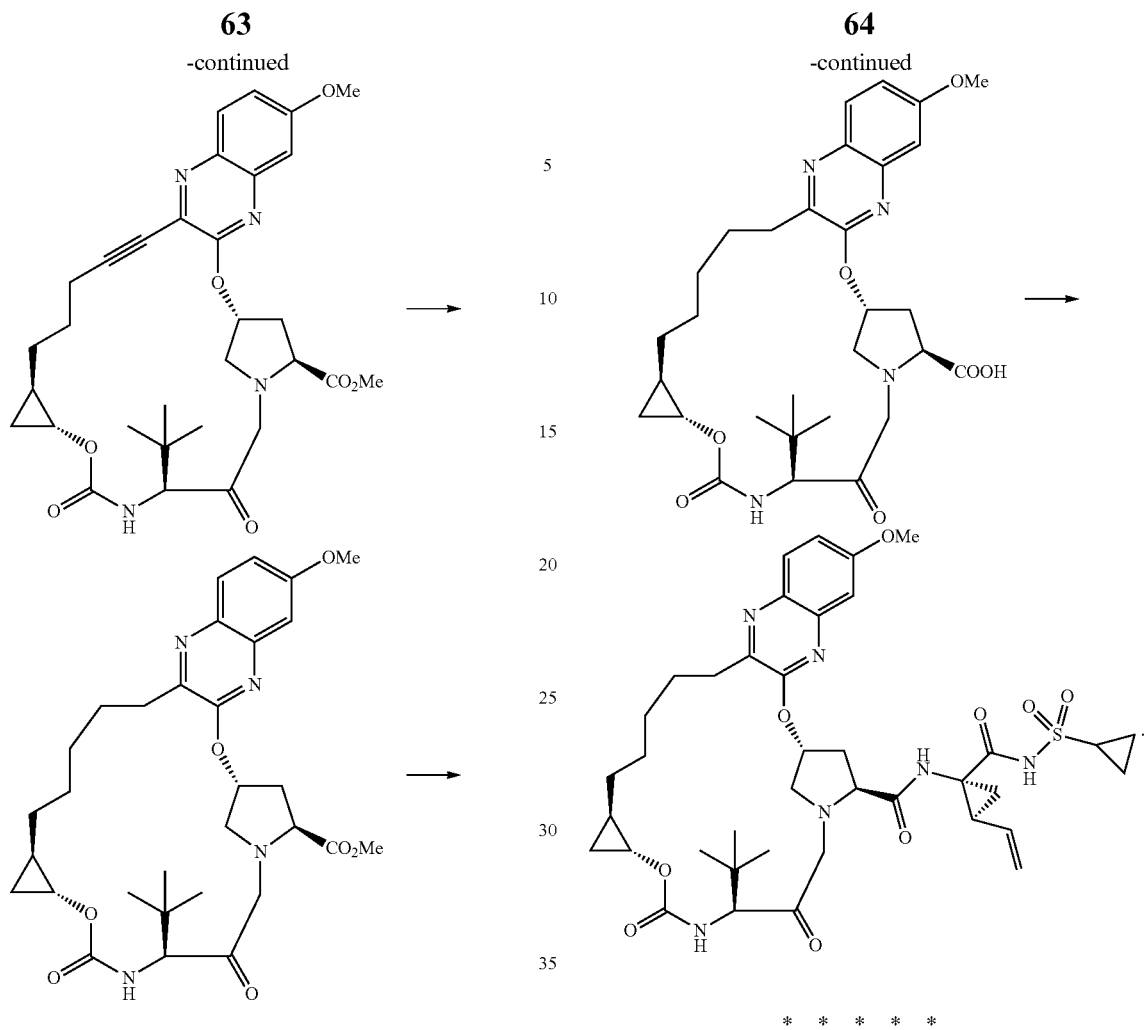

What is claimed is:

1. A method of making compounds of Formula C:

wherein n is selected from the group consisting of 0, 1, 2, 3, 4, 5, 6, 7 and 8; $X^1$ and $X^2$ are each independently selected from the group consisting of Br, Cl and I; and $R^5$ is $CF_3$; said method comprising:

(1) reacting

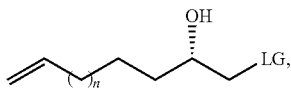

where LG is selected from the group consisting of halogen atoms, $—O—SO_2R^8$, $—O—PO(OR^8)_2$ and a protecting group and each $R^8$ is independently selected from the group consisting of $C_{1-8}$ alkyl, $C_{3-8}$ cycloalkyl, aryl and heteroaryl groups and each $R^8$ is independently substituted by 0, 1, 2, 3 or 4 substituents independently selected from the group consisting of $C_{1-6}$ alkyl, $C_{2-6}$ alkenyl, $C_{2-6}$ alkynyl, aryl, halogen, $—NH_2$ and $—OH$, and the protecting group is selected from $—OSiR^8$ and $—OR^8$, with a chiral alcohol and

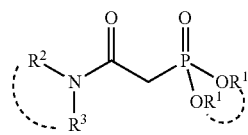

to produce

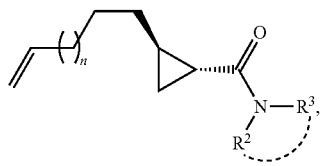

where each $R^1$ is independently selected from the group consisting of $C_{1-8}$ alkyl, aryl and heteroaryl groups, or two $R^1$ are taken, together with the O—P—O atoms to which they are attached, to form a ring containing 5-19 atoms; and where $R^2$ and $R^3$ are each selected from the group consisting of H, $C_{1-8}$ alkyl and $—O—C_{1-8}$ alkyl groups, or $R^2$ and $R^3$ are taken together with the nitrogen atom to which they are attached to form a ring containing 5-19 atoms;

(2) reacting

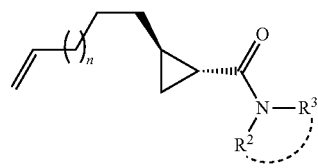

with a Grignard reagent to produce

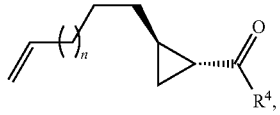

where R⁴ is selected from the group consisting of $C_{1-8}$ alkyl, aryl, and heteroaryl groups and R⁴ is substituted by 0, 1, 2, 3 or 4 substituents independently selected from the group consisting of $C_{1-6}$ alkyl, $C_{2-6}$ alkenyl, $C_{2-6}$ alkynyl, aryl, halogen, —NH₂ or —OH;

(3) halogenating

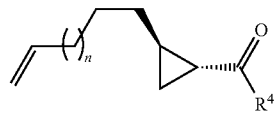

to produce

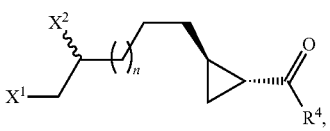

where X¹ and X² are each independently selected from the group consisting of Br, Cl and I; and (4) reacting

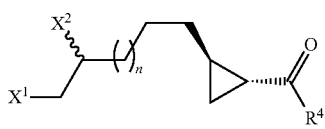

with triflouroacetic anhydride to produce

where R⁵ is CF₃.

2. A method of making a compound of Formula B:

or a salt thereof, wherein n is selected from the group consisting of 0, 1, 2, 3, 4, 5, 6, 7 and 8; and R⁷ is selected from the group consisting of acetyl and

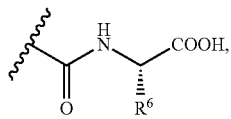

and R⁶ is selected from the group consisting of $C_{1-8}$ alkyl, $C_{3-8}$ cycloalkyl, aryl, and heterocycle groups and R⁶ is substituted by 0, 1, 2, 3 or 4 substituents independently selected from the group consisting of $C_{1-6}$ alkyl, $C_{2-6}$ alkenyl, $C_{2-6}$ alkynyl, aryl, halogen, —NH₂ and —OH, and salts thereof; said method comprising:

preparing a compound of Formula C according to the method of claim 1; and converting

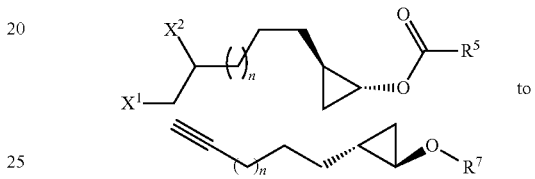

or a salt thereof.

3. The method of claim 1, wherein

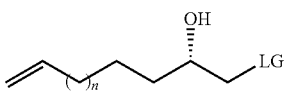

in step (1) is prepared by:

(i) reacting

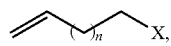

where n is as defined in claim 1 and X is a halogen atom, with a magnesium source to produce

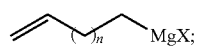

and (ii) reacting

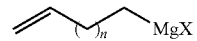

with

to produce

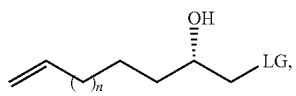

where LG is defined as in claim 1.

4. The method of claim 3, wherein X is Br.

5. The method of claim 2, wherein said converting

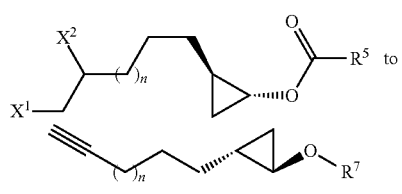

comprises:
(i) de-halogenating

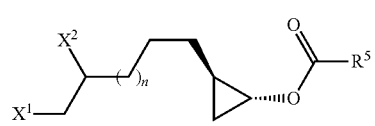

to produce

(ii) reacting

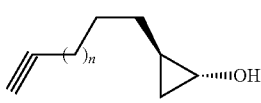

with a reagent containing a leaving group to produce

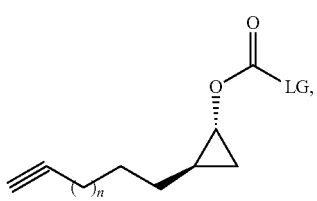

where LG is said leaving group and is selected from the group consisting of halogen atoms, —O—SO$_2$R$^8$, —O—PO(OR$^8$)$_2$ and a protecting group and each R$^8$ is independently selected from the group consisting of C$_{1-8}$alkyl, C$_{3-8}$cycloalkyl, aryl, and heteroaryl groups and each R$^8$ is independently substituted by 0, 1, 2, 3, or 4 substituents independently selected from the group consisting of C$_{1-6}$alky, C$_{2-6}$alkenyl, C$_{2-6}$alkynyl, aryl halogen, —NH$_2$, and —OH, and the protecting group is slected from —OSiR$^8$ and —OR$^8$;

(iii) reacting

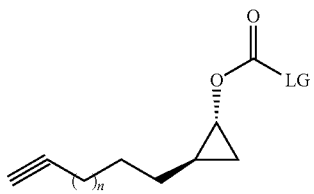

with

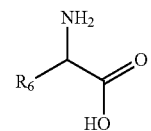

to produce

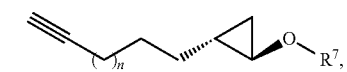

wherein R$^7$ is

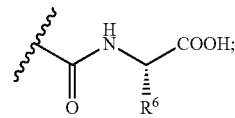

and
(iv) optionally forming a salt of

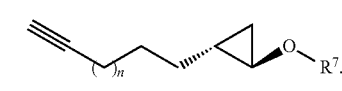

6. The method of claim 2, wherein R$^6$ is selected from the group consisting of C$_2$C$_6$ alykl groups.

7. The method of claim 2, wherein R$^6$ is tert-butyl.

8. The method of claim 1, wherein LG is Cl.

9. The method of claim 1, wherein, in step (1), the chiral alcohol is chlorohydrin.

10. The method of claim 1, wherein, in step (1),

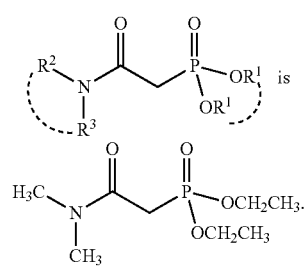

is

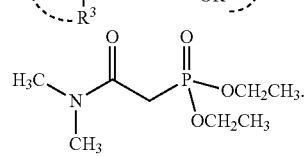

11. The method of claim 5, wherein step (iv) comprises forming a salt of the compound, wherein the salt is selected from tert-butylamine salt, dibenzylamine salt, and dicyclohexyl amine salt.

12. The method of claim 2, wherein the compound of Formula B has the following structural formula:

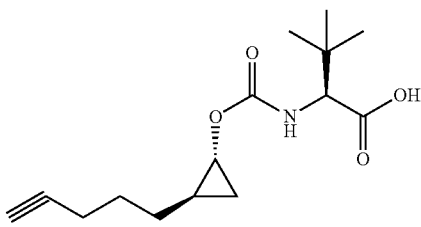 [SMILES: C#CCCC[C@@H]1C[C@H]1OC(=O)N[C@H](C(=O)O)C(C)(C)C]

or a salt thereof, said method comprising:

(1) reacting

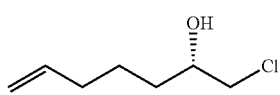

with chlorohydrin and

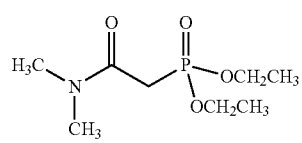

to produce

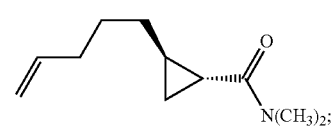

(2) reacting

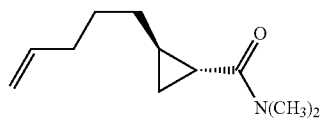

with a Grignard reagent to produce

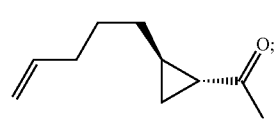

(3) brominating

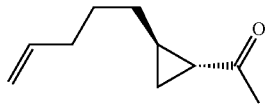

to produce

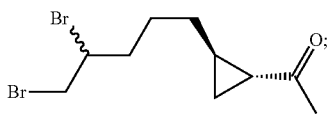

(4) reacting

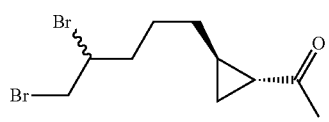

with trifluoroacetic anhydride to produce

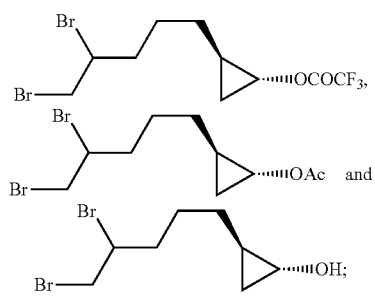

(5) converting

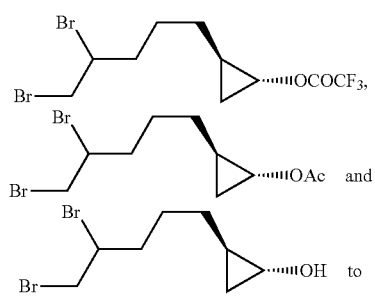

to